(12) United States Patent
Sun et al.

(10) Patent No.: US 11,839,384 B2
(45) Date of Patent: Dec. 12, 2023

(54) POSITION CORRECTION METHOD OF OSTEOTOMY GUIDE TOOL

(71) Applicant: Suzhou MicroPort Orthobot Co., Ltd., Jiangsu (CN)

(72) Inventors: Feng Sun, Jiangsu (CN); Fangqiu Hu, Jiangsu (CN); Chao He, Jiangsu (CN); Tao Li, Jiangsu (CN); Pengfei Liu, Jiangsu (CN)

(73) Assignee: SUZHOU MICROPORT ORTHOBOT CO., LTD., Jiangsu (CN)

(*) Notice: Subject to any disclaimer, the term of this patent is extended or adjusted under 35 U.S.C. 154(b) by 191 days.

(21) Appl. No.: 17/533,986

(22) Filed: Nov. 23, 2021

(65) Prior Publication Data

US 2022/0079603 A1    Mar. 17, 2022

Related U.S. Application Data

(62) Division of application No. 16/859,291, filed on Apr. 27, 2020, now Pat. No. 11,224,442.

(30) Foreign Application Priority Data

Sep. 30, 2019   (CN) .......................... 201910940234.7

(51) Int. Cl.
*A61B 17/15* (2006.01)
*A61B 34/20* (2016.01)
*A61B 34/30* (2016.01)

(52) U.S. Cl.
CPC .......... *A61B 17/151* (2013.01); *A61B 17/154* (2013.01); *A61B 34/20* (2016.02); *A61B 34/30* (2016.02); *A61B 2034/2055* (2016.02)

(58) Field of Classification Search
CPC ....... A61B 34/20; A61B 34/30; A61B 17/151; A61B 17/154
See application file for complete search history.

(56) References Cited

U.S. PATENT DOCUMENTS

2018/0085135 A1   3/2018 Singh
2021/0068845 A1*  3/2021 Schers .................. A61B 34/20

FOREIGN PATENT DOCUMENTS

CN   105813592 A   7/2016
CN   107405170 A   11/2017
(Continued)

*Primary Examiner* — Sameh R Boles
(74) *Attorney, Agent, or Firm* — MUNCY, GEISSLER, OLDS & LOWE, P.C.

(57) ABSTRACT

A method for correcting position of an osteotomy guide tool is disclosed. A trackable element mounted on the osteotomy guide tool or on the robotic arm tracks the position of the osteotomy guide tool and generates position information of the trackable element. According to the current position and the desired position of the trackable element, a robotic arm drives the osteotomy guide tool and the trackable element to move, until the trackable element is moved to the desired position. This method does not need to consider the absolute position accuracy of the robotic arm, and does not rely on the experience of the surgeon. The tool has several guiding features, which can provide guides for osteotomy operations, so that the same osteotomy guide tool can perform multiple operations of osteotomy and punching, thus greatly reducing the operation time and improving the operation efficiency.

9 Claims, 14 Drawing Sheets

(56) References Cited

FOREIGN PATENT DOCUMENTS

| | | |
|---|---|---|
| CN | 108348294 A | 7/2018 |
| CN | 108714049 A | 10/2018 |
| CN | 109620348 A | 4/2019 |
| CN | 109925055 A | 6/2019 |
| CN | 110023729 A | 7/2019 |
| CN | 1-10114031 A | 8/2019 |
| CN | 110711029 A | 1/2020 |

* cited by examiner

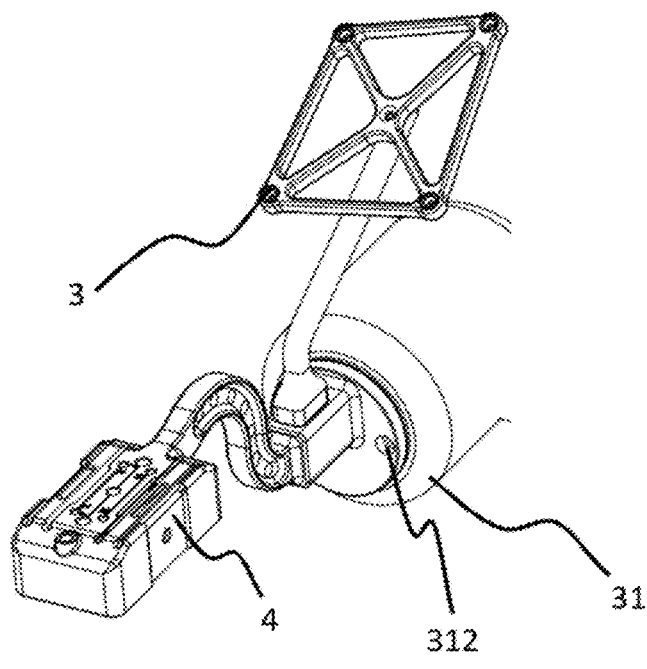
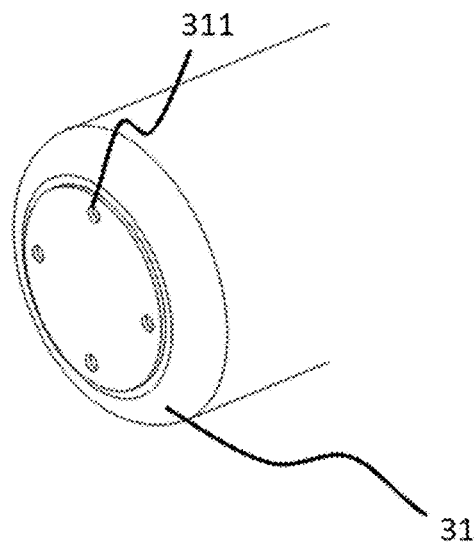
FIG. 26a
FIG. 26b

POSITION CORRECTION METHOD OF OSTEOTOMY GUIDE TOOL

CROSS-REFERENCE TO RELATED APPLICATION

This application is a divisional of U.S. patent application Ser. No. 16/859,291, filed Apr. 27, 2020, which application claims the priority of Chinese patent application number 201910940234.7, filed on Sep. 30, 2019, the entire contents of which are incorporated herein by reference.

TECHNICAL FIELD

The present disclosure relates to the field of robot-assisted surgical systems and methods, and in particular, to a method for correcting position of an osteotomy guide tool, a computer-readable storage medium, an orthopedic surgical system and an osteotomy guide tool.

BACKGROUND

In artificial joint replacement surgeries, various positioners, guides and other tools are used in an osteotomy process before installation of the artificial joint to ensure the accuracy of the osteotomy. Different approaches have been proposed to assist surgeons achieve positioning of the osteotomy guide tools during total knee joint replacement (TKR) surgery.

However, the existing devices or methods for positioning osteotomy guide tools during surgery still have defects such as insufficient positioning accuracy. Therefore, it is necessary to develop methods and surgical systems capable of improving the positioning accuracy of the osteotomy guide tools.

SUMMARY OF THE INVENTION

In view of the above, an objective of the present disclosure is to provide a method for correcting a position of an osteotomy guide tool, a computer-readable storage medium, an orthopedic surgical system and an osteotomy guide tool, in which the real-time position and the pose of the osteotomy guide tool are tracked and fed back, and the movement of the osteotomy guide tool is controlled by a robotic arm to realize the positioning of the osteotomy guide tool and improve the positioning accuracy of the osteotomy guide tool.

In one aspect, the present disclosure provides a method for correcting a position of an osteotomy guide tool, including:

controlling a movement of a robotic arm according to a current position and a desired position of a trackable element, the trackable element mounted on the osteotomy guide tool or on the robotic arm, so that the robotic arm drives the osteotomy guide tool and the trackable element to move, until the trackable element is moved to the desired position;

wherein, a position information of the trackable element is used to represent a position of the osteotomy guide tool.

Optionally, the method for correcting a position of an osteotomy guide tool further includes, before the controlling step, a verificating step for detecting whether the osteotomy guide tool and/or the trackable element is deformed, wherein the verificating step includes:

determining whether an original position of a verification element matches a current position of the verification element based on: i) the original position of the verification element mounted on the osteotomy guide tool relative to the trackable element before leaving a factory, and ii) the current position of the verification element relative to the trackable element during use of the osteotomy guide tool;

determining that the osteotomy guide tool and/or the trackable element is not deformed if the original position of the verification element matches the current position of the verification element, and proceeding to the controlling step of controlling the movement of the robotic arm according to the current position and the desired position of the trackable element mounted on the osteotomy guide tool or on the robotic arm; and determining that the osteotomy guide tool and/or the trackable element is deformed if the original position of the verification element does not match the current position of the verification element, and correcting a relative position between the osteotomy guide tool and the trackable element before proceeding to the controlling step of controlling the movement of the robotic arm according to the current position and the desired position of the trackable element mounted on the osteotomy guide tool or on the robotic arm.

Optionally, in the position correction method, the correcting step includes:

acquiring positions of at least two correction elements mounted on the osteotomy guide tool relative to the trackable element; and obtaining a current position of the osteotomy guide tool relative to the trackable element according to the positions of the at least two correction elements relative to the trackable element, and updating the relative position between the osteotomy guide tool and the trackable element.

Optionally, in the position correction method, the positions of two of the correction elements relative to the trackable element are recorded as $T_1$ and $T_2$ where $T_1$ represents a position of a first correction element in a coordinate system of the trackable element, and $T_2$ represents a position of a second correction element in the coordinate system of the trackable element;

wherein the current position of the osteotomy guide tool relative to the trackable element is obtained by:

obtaining a position $T_0$ of a center point of an osteotomy guide block and a position $T_3$ of a surface of the osteotomy guide block in the coordinate system of the trackable element, according to the positions $T_1$ and $T_2$ of the at least two correction elements in the coordinate system of the trackable element; and obtaining a position and a pose of the osteotomy guide tool relative to the trackable element according to the position $T_0$ of the center point of the osteotomy guide block and the position $T_3$ of the surface of the osteotomy guide block in the coordinate system of the trackable element.

Optionally, in the position correction method, before the controlling step, the method further includes:

determining a desired moving path of the trackable element according to the current position and the desired position of the trackable element;

wherein during the controlling step, the robotic arm is controlled to move the trackable element from the current position to the desired position along the desired moving path.

Optionally, in the position correction method, the desired position of the trackable element is obtained according to a posture mapping relationship between the trackable element and the osteotomy guide tool, as well as a target position of the osteotomy guide tool.

Optionally, in the position correction method, the posture mapping relationship between the trackable element and the osteotomy guide tool includes a posture mapping relationship between multiple guiding features on the osteotomy guide tool and the trackable element.

Optionally, in the position correction method, the posture mapping relationship between each of the multiple guiding features and the trackable element is obtained by:

acquiring relative positions between respective target balls on the trackable element, and establishing a coordinate system of the trackable element according to the acquired relative positions;

acquiring a position of a center point of an osteotomy guide block in the coordinate system of the trackable element; and determining a position and a pose of the multiple guiding features in the coordinate system of the trackable element according to positions of the multiple guiding features relative to the center point of the osteotomy guide, as well as a position of the center point of the osteotomy guide in the coordinate system of the trackable element.

In another aspect, the present disclosure provides a computer-readable storage medium having an instruction thereon, wherein a method for correcting a position of an osteotomy guide tool is performed when the instruction is executed by a processor, the method for correcting a position of an osteotomy guide tool including:

controlling a movement of a robotic arm according to a current position and a desired position of a trackable element mounted on the osteotomy guide tool or on the robotic arm, so that the robotic arm drives the osteotomy guide tool and the trackable element to move, until the trackable element is moved to the desired position; wherein a position of the trackable element is used to represent a position of the osteotomy guide tool.

In still another aspect, the present disclosure provides an orthopaedic surgical system includes a control device, a navigation device, a robotic arm and an osteotomy guide tool, wherein a tail end of the robotic arm is connected to the osteotomy guide tool, and the robotic arm is configured to adjust a position and a pose of the osteotomy guide tool;

wherein the navigation device includes a tracker and a trackable element, the trackable element is configured to be mounted on the osteotomy guide tool or on the robotic arm, and the tracker is configured to track and generate a current position information of the trackable element which is used to represent a position of the osteotomy guide tool;

wherein the control device includes a computer-readable storage medium storing an instruction, wherein a method for correcting a position of an osteotomy guide tool is performed when the instruction is executed by a processor, the method for correcting a position of an osteotomy guide tool including:

controlling a movement of the robotic arm according to the current position of the trackable element fed back by the tracker and a desired position of the trackable element, so that the robotic arm drives the osteotomy guide tool and the trackable element to move until the trackable element is moved to the desired position.

Optionally, in the orthopaedic surgical system, the orthopaedic surgical system further includes a verification device for verifying whether the osteotomy guide tool and/or the trackable element is deformed;

wherein the osteotomy guide tool includes an osteotomy guide block, and the osteotomy guide block is provided with a plurality of guiding features configured to provide guidance for an osteotomy operation, the verification device includes at least one verification element configured to be detachably mounted on the osteotomy guide block;

wherein the tracker is configured to record an original position of the verification element relative to the trackable element before leaving a factory, and the tracker is configured to record a current position of the verification element relative to the trackable element before each operation;

wherein the control device is configured to determine whether the original position of the verification element matches the current position of the verification element; if the original position of the verification element matches the current position of the verification element, the osteotomy guide tool and/or the trackable element is determined as not deformed; if the original position of the verification element does not match the current position of the verification element, the osteotomy guide tool and/or the trackable element is determined as deformed.

Optionally, in the orthopedic surgical system, the orthopedic surgical system further includes a correction device, which is configured to correct the relative position between the osteotomy guide tool and the trackable element when the verification device determines that the osteotomy guide tool and/or the trackable element is deformed; wherein the correction device includes at least two correction elements detachably mounted on the osteotomy guide block;

wherein the tracker is configured to record positions of the at least two correction elements relative to the trackable element; and wherein the control device is configured to obtain a current position of the osteotomy guide tool relative to the trackable element according to the positions of the at least two correction elements relative to the trackable element, and update the relative position between the osteotomy guide tool and the trackable element.

Optionally, in the orthopedic surgical system, the positions of two of the correction elements relative to the trackable element are recorded as $T_1$ and $T_2$, where $T_1$ represents a position of a first correction element in a coordinate system of the trackable element, and $T_2$ represents a position of a second correction element in the coordinate system of the trackable element;

wherein: the control device is configured to obtain a position $T_0$ of a center point of the osteotomy guide block and a position $T_3$ of a surface of the osteotomy guide block in the coordinate system of the trackable element according to the positions $T_1$ and $T_2$ of the at least two correction elements in the coordinate system of the trackable element; wherein the control device is further configured to obtain a position and a pose of the osteotomy guide tool relative to the trackable element according to the position $T_0$ of the center point of the osteotomy guide block and the position $T_3$ of the surface of the osteotomy guide block in the coordinate system of the trackable element.

Optionally, in the orthopedic surgical system, the navigation device further includes a basal target, the basal target is fixed in position and the position of the trackable element refers to the position of the trackable element relative to the basal target.

Optionally, in the orthopedic surgical system, the control device is configured to provide a desired moving path composed of a plurality of positioning points, and the control device is configured to control the movement of the robotic arm so as to move the trackable element to the desired position along the desired moving path.

Optionally, in the orthopedic surgical system, the orthopedic surgical system further includes a storage device for storing a posture mapping relationship between the trackable element and the osteotomy guide tool.

Optionally, in the orthopedic surgical system, the osteotomy guide includes an osteotomy guide block, and the osteotomy guide is provided with multiple guiding features configured to provide guidance for an osteotomy operation; wherein the posture mapping relationship between the trackable element and the osteotomy guide tool includes a posture mapping relationship between the multiple guiding features and the trackable element.

Optionally, in the orthopaedic surgical system, the posture mapping relationship between each of the multiple guiding features and the trackable element is obtained by:

acquiring relative positions between respective target balls on the trackable element, and establishing a coordinate system of the trackable element according to the acquired relative positions;

acquiring a position of a center point of an osteotomy guide block in the coordinate system of the trackable element; and determining a position and a pose of the plurality of guiding features in the coordinate system of the trackable element according to positions of the multiple guiding features relative to the center point of the osteotomy guide, as well as a position of the center point of the osteotomy guide in the coordinate system of the trackable element.

Optionally, in the orthopedic surgical system, the osteotomy guide block is provided with at least one verification hole, and the verification element is mounted on the verification hole; the verification element has a step, and a stepped surface of the step is parallel to a surface of the osteotomy guide block.

Optionally, in the orthopedic surgical system, the osteotomy guide block has an upper surface, and the multiple guiding features are provided on the upper surface; wherein the verification hole vertically extends from the upper surface, and the stepped surface matches the upper surface.

Optionally, in the orthopedic surgical system, an axis of the verification hole is located on a symmetry plane of the osteotomy guide block, and wherein an end surface of the verification hole, the upper surface of the osteotomy guide block and the stepped surface are coplanar.

Optionally, in the orthopedic surgical system, a position information of the verification element relative to the trackable element includes: a position and a pose of a front end of the verification element in a coordinate system of the trackable element.

Optionally, in the orthopedic surgical system, the position of each of the correction elements in the coordinate system of the trackable element includes:

a position and a pose of a front end of the correction element in the coordinate system of the trackable element; and a position and a pose of a stepped surface of the correction element in the coordinate system of the trackable element;

wherein the correction element has a step, and the stepped surface of the step is parallel to a surface of the osteotomy guide block.

Optionally, in the orthopedic surgical system, the osteotomy guide block is provided with a correction hole, two of the correction elements are both mounted on the correction hole, or two of the correction elements are respectively mounted on the verification hole and the correction hole.

Optionally, in the orthopedic surgical system, an end surface of the correction hole is coplanar with a corresponding surface of the osteotomy guide block and the stepped surface of the correction element.

Optionally, in the orthopedic surgical system, the osteotomy guide tool includes an osteotomy guide block and a mounting interface, wherein the mounting interface is connected to the osteotomy guide block via a connecting shaft, the osteotomy guide block is provided with multiple guiding features configured to provide guidance for an osteotomy operation, and the mounting interface is further detachably connected to the tail end of the robotic arm.

Optionally, in the orthopedic surgical system, the connecting shaft is an eccentric crank connected to the osteotomy guide block and the mounting interface, respectively, and wherein a rotation axis of the mounting interface is offset from a rotation axis of the osteotomy guide block.

Optionally, in the orthopedic surgical system, the osteotomy guide tool further includes a mounting base, wherein the osteotomy guide block, the eccentric crank, the mounting base and the mounting interface are connected in sequence, and the mounting base is provided with a target mounting hole.

Optionally, in the orthopedic surgical system, the osteotomy guide block is detachably connected to the eccentric crank.

Optionally, in the orthopedic surgical system, the guiding feature includes multiple guiding grooves, the multiple guiding grooves are distributed on a same surface of the osteotomy guide block, or the multiple guiding grooves are arranged on different surfaces around an axis of the osteotomy guide block.

Optionally, in the orthopedic surgical system, the multiple guiding groove are 0° guiding grooves or 45° guiding grooves.

Optionally, in the orthopedic surgical system, the osteotomy guide tool includes two osteotomy guide blocks mirrored to each other, and each osteotomy guide block is provided with a quick-change interface for detachably connecting to the eccentric crank.

Optionally, in the orthopedic surgical system, the osteotomy guide tool includes an osteotomy guide block, the osteotomy guide block is provided with two mounting interfaces that are oppositely disposed, and the eccentric crank is detachably connectable to any one of the two mounting interfaces.

Optionally, in the orthopaedic surgical system, the orthopaedic surgical system further includes a sterile bag sleeved on the tail end of the robotic arm, and wherein one end of the sterile bag covers a connection port of the robotic arm, the connection port is detachably connectable to the osteotomy guide tool.

Optionally, in the orthopaedic surgical system, an end of the sterile bag is provided with a yield hole.

In still another aspect, the present disclosure provides an osteotomy guide tool for the orthopaedic surgical system as described above, and the osteotomy guide tool includes an osteotomy guide block, a connecting shaft and a mounting interface; the osteotomy guide block is provided with multiple guiding features configured to provide guidance for an osteotomy operation; wherein two ends of the connecting shaft are respectively connected to the osteotomy guide block and the mounting interface, and the mounting interface is configured to be detachably connected to the tail end of the robotic arm.

Optionally, in the osteotomy guide tool, the multiple guiding features include a guiding groove and a guiding hole.

Optionally, in the osteotomy guide tool, the connecting shaft is an eccentric crank.

Optionally, in the osteotomy guide tool, the osteotomy guide tool further includes a mounting base, wherein the osteotomy guide block, the eccentric crank, the mounting base and the mounting interface are sequentially connected, and the mounting base is provided with a target mounting hole.

Optionally, in the osteotomy guide tool, the osteotomy guide block is detachably connected to the eccentric crank.

Optionally, in the osteotomy guide tool, both ends of the guiding groove penetrate a surface of the osteotomy guide block to form a breach.

Optionally, in the osteotomy guide tool, the guiding groove has a shape of a horn.

Optionally, in the osteotomy guide tool, a plurality of guiding grooves are provided, and the plurality of guiding grooves are arranged on different surfaces around the axis of the osteotomy guide block.

Optionally, the plurality of guiding grooves are 0° guiding grooves or 45° guiding grooves.

Optionally, in the osteotomy guide tool, the guiding groove includes at least one of a 0° guiding groove; a 45° guiding groove; and a pulley-osteotomy groove; the guiding hole includes at least one of a femoral prosthesis-mounting guiding hole, a left leg tibial-tooling positioning guiding hole, a right leg tibial-tooling positioning guiding hole and an osteotomy-guide fixing hole.

Optionally, in the osteotomy guide tool, the guiding groove includes two 0° guiding grooves, two 45° guiding grooves and two pulley-osteotomy grooves.

Optionally, in the osteotomy guide tool, the osteotomy guide block has an axisymmetric structure.

Optionally, in the osteotomy guide tool, the osteotomy guide block is provided with two mounting interfaces, the two mounting interfaces are oppositely disposed, and the eccentric crank is detachably connectable to any one of the two mounting interfaces.

Optionally, in the osteotomy guide tool, the osteotomy guide block is provided with a verification hole.

Optionally, in the osteotomy guide tool, the osteotomy guide block is provided a correction hole.

The position correction method in the present disclosure comprises tracking and feeding back the real-time pose of the osteotomy guide tool, and controlling the movement of the robotic arm according to the real-time pose of the osteotomy guide tool. It is unnecessary for the method to consider the absolute position accuracy of the robotic arm itself, and to rely on the experience of the surgeon, making the position of the osteotomy guide tool more accurate and improving the positioning accuracy of the osteotomy guide tool. In addition, the above-mentioned orthopedic surgical system suspends the osteotomy guide tool by a robotic arm without fixing the tool to the human body, which can avoid secondary injury to the human body.

The position correction method in the present disclosure also checks whether the osteotomy guide tool and/or trackable element is deformed by verifying the trackable element, so that any deformed osteotomy guide tool and/or trackable element can be timely and conveniently replaced or corrected, thereby reducing the risk of surgery and improving surgery accuracy. For example, the above-mentioned position correction method also corrects and updates the relative positional relationship between the osteotomy guide tool and the trackable element via at least two correction elements, and the correction process is simple and convenient.

The osteotomy guide tool in the present disclosure includes an osteotomy guide block, and the osteotomy guide block is provided with a plurality of guiding features. These guiding features are designed with different combinations of guiding holes and guiding grooves, which can provide a variety of guidance for osteotomy, so that the same osteotomy guide tool can perform multiple operations of osteotomy and punching. There is no need to frequently change the osteotomy guide tool during the operation, which can greatly reduce the operation time and improve the operation efficiency.

The above osteotomy guide tool optionally has an axisymmetric structure, so that the same osteotomy guide tool can take into account both left and right limbs, thus reducing costs, simplifying osteotomy operations, and improving surgical efficiency.

The guiding groove in the osteotomy guide tool, for example, the 45° guiding groove or the 0° guiding groove, has two ends penetrating the surface of the osteotomy guide block to form a bevel, which enables the osteotomy guide tool to be used for osteotomy guide of different types of prostheses.

The guiding groove in the osteotomy guide tool, for example, the 0° guiding groove or the 45° guiding groove, has a shape of a horn, which enables the osteotomy guide tool to be used for osteotomy guide of different types of prostheses.

The guiding groove in the osteotomy guide tool, for example, the 0° guiding groove or the 45° guiding groove, is optionally distributed on different surfaces around the axis of the osteotomy guide block. In this way, the amplitude of adjustment of the osteotomy guide tool when cutting different osteotomy surfaces can be reduced, and the problem of increased pose recognition error or failure of recognition caused by a too large rotation amplitude of the trackable element can be prevented. At the same time, a large transmission error caused by the excessive change of the pose of the robotic arm can also be avoided, thereby further improving the positioning accuracy.

The rotation axis of the osteotomy guide tool and the rotation axis of the end joint of the robotic arm are eccentric. As such, the robotic arm only needs to perform a small linear displacement and rotation when adjusting the angle of the osteotomy guide tool, which can reduce the transmission error of the robotic arm and improve the positioning accuracy.

BRIEF DESCRIPTION OF DRAWINGS

The implementation method of the present disclosure and the features, properties, and advantages of the related embodiments will be described by referring to the following drawings, in which:

FIG. 26a is a schematic structural diagram of a sterile bag sleeved on an end joint of a robotic arm according to an embodiment of the present disclosure;

FIG. 26b is a partially enlarged view of an avoidance hole provided at one end of a sterile bag according to an embodiment of the present disclosure.

Figure 1:
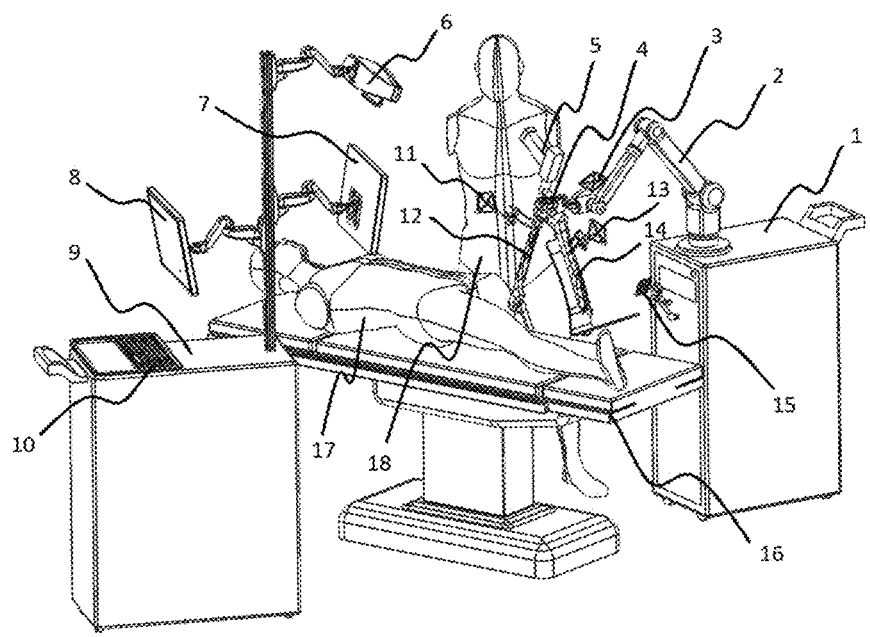
FIG. 1 is a schematic diagram of knee joint replacement using an orthopaedic surgical system according to an embodiment of the present disclosure.

In the figures:
1-surgical trolley; 2-robotic arm; 3-trackable element; 4-osteotomy guide tool; 5-surgical tool; 6-tracker; 7-auxiliary display; 8-main display; 9-navigation trolley; 10-keyboard; 11-femoral target; 12-femur; 13-tibia target; 14-tibia; 15-basal target; 16-verification element; 17-patient; 18-surgeon;

40, 41, 42, 43, 20, 21, 22, 23, 24, 25, 26, 27, 28, 29, 30-osteotomy guide block;

401-mounting interface; 402-mounting base; 4021-target mounting hole; 403-eccentric crank; 404-femoral prosthesis mounting guiding hole; 405-right leg pulley-osteotomy groove; 406-left leg tibial-tooling positioning guiding hole; 407-first 0° guiding groove; 408-first 45° guiding groove; 409-verification hole; 410-second 45° guiding groove; 411-second 0° guiding groove; 412-left leg pulley-osteotomy groove; 413-right leg tibial-tooling positioning guiding hole; 414a-first correction hole; 414b-second correction hole;

415, 421, 431, 432-quick-change interface; 201, 211-0° guiding groove; 221-pulley-osteotomy groove; 231, 241, 251, 271-guiding hole; 261-locating hole; 272-square groove; 273-long guiding groove; 281-breach; 31-sterile bag; 311-yielding hole; 312-fastener.

DETAILED DESCRIPTION OF EXEMPLARY EMBODIMENTS

In the following, the technical solutions in the embodiments of the present disclosure will be clearly and completely described with reference to the drawings in the embodiments of the present disclosure. Obviously, the described embodiments are some embodiments of the present disclosure, but not all of the embodiments of the present disclosure. Based on the embodiments of the present disclosure, all other embodiments obtained by those skilled in the art without creative efforts shall fall within the protection scope of the present disclosure.

As used in the present disclosure, the singular forms "a", "an" and "the" include plural referents unless the content clearly dictates otherwise. As used in the present disclosure, the term "or" is generally used in its sense including "and/or" unless the content clearly dictates otherwise. As used in the present disclosure, the term "several" is generally used in its sense including "at least one" unless the content clearly indicates otherwise. As used in the present disclosure, the term "at least two" is generally used in its sense including "two or more" unless the content clearly indicates otherwise. In addition, the terms "first", "second" and "third" are used for descriptive purposes only, and cannot be understood as indicating or implying relative importance or implicitly indicating the number of technical features indicated. Therefore, the features defined as "first", "second" and "third" may explicitly or implicitly include one or at least two of the features.

The present disclosure is to provide a position correction method of an osteotomy guide tool. The idea of position correction is to use the trackable element mounted on the osteotomy guide tool or on the robotic arm to track the position of the osteotomy guide tool, and then as long as the position information of the trackable element is obtained, the movement of the robotic arm can be controlled according to the position information of the trackable element (including the current position and the desired position of the trackable element), so that the robotic arm drives the osteotomy guide tool and the trackable element to move, until the trackable element is moved to the desired position. Because there is a mapping relationship between the position of the trackable element and the position of the osteotomy guide tool, adjusting the position and the pose of the trackable element is equivalent to adjusting the position and the pose of the osteotomy guide tool, that is, the position of the trackable element is used to represent the position of the osteotomy guide tool. It is unnecessary to take into account the absolute position accuracy of the robotic arm itself, and to rely on the experience of a surgeon, thereby making the position of the osteotomy guide tool more accurate, and improving the positioning accuracy and surgical accuracy of the osteotomy guide tool.

In order to achieve the precise positioning of the osteotomy guide tool, the present disclosure is also to provide an orthopaedic surgical system including a control device, a navigation device, a robotic arm and an osteotomy guide tool (or a cut guide). The end of the robotic arm is connected to the osteotomy guide tool or the cut guide. The robotic arm is configured to adjust the position and the pose (referred to the posture) of the osteotomy guide tool. The navigation device includes a tracker and a trackable element. The trackable element is mounted on the osteotomy guide tool or on a robotic arm, and the tracker is configured to track the current position of the trackable element and generate the current position information. Therefore, in actual use, the control device is configured to control the movement of the robotic arm according to the current position information and the desired position information of the trackable element fed back by the tracker, so that the robotic arm drives the osteotomy guide tool and the trackable element to move, until the trackable element is moved to the desired position. In addition to the advantages described above, the orthopaedic surgical system of the present disclosure can also suspend the osteotomy guide tool through a robotic arm without fixing the tool to the human body, and can avoid secondary injury to the human body.

However, the application environment of the orthopaedic surgical system of the present disclosure is not particularly limited. For example, it can be applied to knee joint replacement or other orthopedic surgery. In the following description, an orthopaedic surgical system is described using knee joint replacement as an example, but it should not be used to limit the present disclosure.

FIG. 1 is a schematic diagram of knee joint replacement using an orthopaedic surgical system according to an embodiment of the present disclosure. As shown in FIG. 1, the orthopedic surgical system includes a control device, a navigation device, a robotic arm 2 and an osteotomy guide tool 4. The control device is actually implemented by a computer which is equipped with a controller, a main display 8 and a keyboard 10, and more preferably the computer is further equipped with an auxiliary display 7. In this embodiment, the contents displayed on the auxiliary display 7 and the contents displayed on the main display 8 are the same, for example, both are used to display osteotomy position images. The navigation device is an electromagnetic positioning navigation device, an optical positioning navigation device, or an electromagnetic positioning navigation device. In some embodiments, the navigation device is an optical positioning navigation device. Compared with other navigation methods, the measurement accuracy of the optical positioning navigation is high, which can effectively improve the positioning accuracy of the osteotomy guide tool.

In the following description, the optical positioning navigation device is taken as an example for description, but is not limited herein.

The navigation device specifically includes a navigation marker and a tracker 6. The navigation marker includes a basal target 15 and a trackable element 3. The basal target 15 is fixed, for example, the basal target 15 is fixed on the surgical trolley 1 such that a base coordinate system (also referred to as a basal target coordinate system) is established. The trackable element 3 is mounted on the osteotomy guide tool 4 to track the position of the osteotomy guide tool 4. The osteotomy guide tool 4 is mounted at the end of the robotic arm 2 so that the osteotomy guide tool 4 is supported by the robotic arm 2 and the spatial position and the pose of the osteotomy guide tool 4 are adjusted.

In practice, the tracker 6 is configured to capture the signal (preferably an optical signal) reflected by the trackable element 3 and record the position of the trackable element 3 (that is, the position and the pose of the trackable element under the base coordinate system). Then the instruction stored in the controller controls the movement of the robotic arm 2 according to the current position and the desired position of the trackable element. The robotic arm 2 drives the osteotomy guide tool 4 and the trackable element 3 to move, until the trackable element 3 is moved to the desired position. The expected position of the trackable element 3 corresponds to the desired position of the osteotomy guide tool 4.

Therefore, the application of the orthopedic surgical system can realize the automatic positioning of the osteotomy guide tool 4, and the trackable element 3 tracks and feeds back the real-time pose of the osteotomy guide tool 4 during the operation. The adjustment of the position and the pose of the osteotomy guide tool is achieved by controlling the movement of the robotic arm. Not only the positioning accuracy of the osteotomy guide tool is high, but also the osteotomy guide tool 4 is supported by the robotic arm 2 without fixing the guide tool on the human body, which can avoid secondary injury to the human body.

Generally, the orthopedic surgical system further includes a surgical trolley 1 and a navigation trolley 9. The control device and a part of the navigation device are mounted on the navigation trolley 9, for example, the controller is mounted inside the navigation trolley 9, and the keyboard 10 is placed outside the navigation trolley 9 for operation. The main display 8, the auxiliary display 7 and the tracker 6 are all mounted on a bracket, the bracket is vertically fixed on the navigation trolley 9, and the robotic arm 2 is mounted on the surgical trolley 1. The use of the surgical trolley 1 and the navigation trolley 9 makes the entire surgical operation more convenient.

When performing knee joint replacement surgery, the use of the orthopedic surgical system of this embodiment generally includes the following operations:

first, moving the surgical trolley 1 and the navigation trolley 9 to appropriate positions next to the hospital bed;

then, providing the navigation markers (the navigation markers also include the femoral target 11, the tibial target 13), the osteotomy guide tool 4 and other related components (such as sterile bags);

after that, the surgeon 18 imports the CT/MR scan model of the bone of the patient 17 into the computer for preoperative planning to obtain an osteotomy scheme. The osteotomy scheme includes, for example, the osteotomy scheme coordinates, the model of the prosthesis, and the installation orientation of the prosthesis. Specifically, based on the patient knee image data obtained from CT/MR scans, then an osteotomy scheme is created based on the three-dimensional digital model of the knee joint, so that the surgeon can perform preoperative evaluation according to the osteotomy scheme. Specifically, the osteotomy scheme is determined based on the three-dimensional digital model of the knee joint, and the obtained prosthesis size specifications and the installation position of the osteotomy plate. The osteotomy scheme is finally output in the form of a surgical report, which records a series of reference data such as the coordinates of the osteotomy plane, the amount of osteotomy, the angle of the osteotomy, the size of the prosthesis, the installation position of the prosthesis, and the surgical aids/assisting tools, especially a series of theoretical explanations, such as the reason for selecting the osteotomy angle to provide a reference for the surgeon. The three-dimensional digital model of the knee joint can be displayed on the main display 8 and the surgeon can enter surgical parameters via the keyboard 10 for preoperative planning.

After the preoperative evaluation, the surgeon 18 then uses a target pen or a pole with tracking elements to mark the guiding features on the patient's femur and the tibia (that is, the surgeon marks multiple femoral anatomical guiding features on the patient's femoral entity and multiple tibial anatomical guiding features on the patient's tibial entity). The navigation device takes the basal target 15 as a reference, records the positions of all guiding features on the patient's tibia 14 and femur 12, and sends the positions information of all guiding features to the controller, and then the controller obtains the actual orientation of the femur 12 and the tibia 14 by means of the feature matching algorithm, and corresponds to the orientation of the CT/MR images on the femur 12 and the tibia 14.

Subsequently, the actual orientation of the femur and the tibia is linked to the corresponding target mounted on the femur and the tibia by the navigation device, so that the femoral target 11 and the tibia target 13 can track the current position of the bone in real time. The relative position between the target and the bone is fixed, the bone movement will not affect the surgical effect.

Further, the coordinate of the osteotomy scheme planned before the operation is sent to the robotic arm 2 by the navigation device. After the robotic arm 2 locates the osteotomy scheme through the trackable element 3 and moves to the predetermined position, the robotic arm 2 is in the holding state (that is, the robotic arm 2 does not move). After that, the surgeon can use the surgical tool 5 such as a pendulum saw or an electric drill to perform osteotomy and/or punching operations by the osteotomy guide tool 4. After the osteotomy and punching operations are completed, the surgeon can install the prosthesis and perform other surgical operations.

In this embodiment, the navigation marker further includes a femur target 11 and a tibial target 13. The femoral target 11 is configured to locate/track the spatial position and the pose of the femur 12, and the tibial target 13 is configured to locate/track the spatial position and the pose of the tibia 14. As mentioned before, the trackable element 3 is mounted on the osteotomy guide tool 4, but in other embodiments, the trackable element 3 is also mounted on the end joint of the robotic arm 2.

Figure 2:
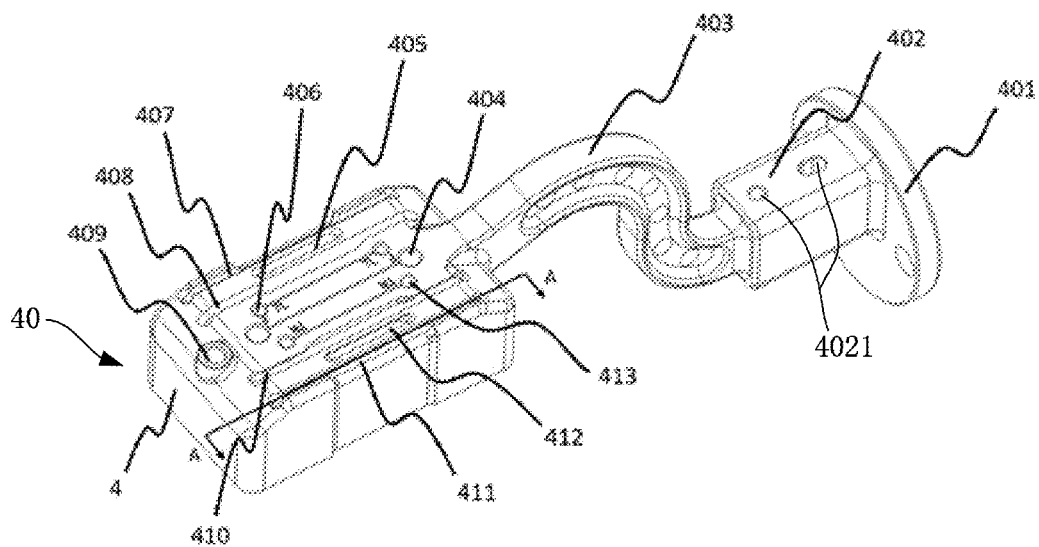
FIG. 2 is a schematic structural diagram of an osteotomy guide tool provided by an embodiment of the present disclosure.

FIG. 2 is a schematic structural diagram of an osteotomy guide tool provided by a an embodiment of the present disclosure. As shown in FIG. 2, the osteotomy guide tool 4 of this embodiment is used for knee joint replacement, and includes an osteotomy guide block 40. The osteotomy guide block 40 is provided with guiding features. The guiding features include a guiding groove or a guiding hole, or a combination of a guiding groove and a guiding hole. That is, the guiding features on the osteotomy guide block 40 may be one or more combinations of the guiding groove and the guiding hole, thereby providing one or more guides for osteotomy of knee replacement, specifically providing guides for osteotomy and punching operations of the distal femur, the front of the femur, the back of the femur, the oblique of the front of the femur, the oblique of the femur, the pulley groove, the femoral prosthesis mounting hole, the tibial plateau, and the tibial keel treatment locating hole, so that the same osteotomy guide tool can perform multiple operations of osteotomy and punching. The osteotomy guide tool does not need to be replaced during the operation, which can greatly reduce the operation time and improve the surgical efficiency.

As mentioned above, the position of the osteotomy guide tool is represented by the position of the trackable element. To achieve this, it is also necessary to calibrate the posture mapping/corresponding relationship between the trackable element 3 and the osteotomy guide tool 4 in advance. In this embodiment, the posture mapping relationship between the trackable element 3 and the osteotomy guide tool 4 includes the posture mapping relationship between all the guiding features and the trackable element 3. For example, when the guiding feature includes a guiding groove and a guiding hole, the posture mapping relationship between the trackable element 3 and the osteotomy guide tool 4 includes: position information of each guiding groove of the osteotomy guide tool 4 in the coordinate system of the trackable element, and the position information of each guiding hole of the osteotomy guide tool 4 in the coordinate system of the trackable element.

In this embodiment, the posture mapping relationship of each guiding feature (such as a guiding groove or a guiding hole) relative to the trackable element 3 can be obtained in the following ways:

Step 1: obtaining the relative positional relationship between the target spheres (mainly for four target spheres) on the trackable element 3 and establishing the coordinate system of the trackable element accordingly;

Step 2: obtaining the coordinates (i.e., position information) of the center point (or geometric center, centroid) of the osteotomy guide block 40 in the coordinate system of the trackable element;

Step 3: according to the position information of the guiding feature relative to the center point of the osteotomy guide block 40 and the coordinate information (or the position information) of the center point of the osteotomy guide block 40 in the coordinate system of the trackable element, obtaining the position information (including position and the pose) of the guiding feature in the coordinate system of the trackable element, and the position information of the guiding feature in the coordinate system of the trackable element refers to posture mapping relationship between the guiding feature and the trackable element 3.

Therefore, it is necessary to calibrate the positions and poses of all guiding features on the osteotomy guide block in the coordinate system of the trackable element and record these data for the controller to retrieve these data for conversion. Preferably, the posture mapping relationship between each of the guiding features and the trackable element can be obtained by performing the above steps by the controller.

With continued reference to FIG. 2, the osteotomy guide tool 4 further includes a mounting interface 401. The mounting interface 401 is connected to the osteotomy guide block 40 via a connecting shaft, and the mounting interface 401 is further detachably connected to the end of the robotic arm 2 in order to realize the connection between the osteotomy guide tool 4 and the robotic arm 2. Further, the mounting interface 401 is a flange. At this time, it can be connected to the flange at the end of the robotic arm by fasteners such as screws and positioning pins. In other embodiments, the mounting interface 401 is a quick-change interface, which is connected to the end of the robotic arm 2 for quick disassembly to achieve the purpose of quick disassembly.

The osteotomy guide tool 4 further includes a connecting shaft, and two ends of the connecting shaft are respectively connected to the osteotomy guide block 40 and the mounting interface 401. As shown in FIG. 2, the connecting shaft is preferably an eccentric crank 403. By using the eccentric crank 403, there can be a certain offset between the rotation axis of the mounting interface 401 (that is, the rotation axis of the end joint of the robotic arm) and the rotation axis of the osteotomy guide block 40, and thus the robotic arm 2 only needs to perform a small linear displacement and rotation when adjusting the angle of the osteotomy guide tool 4 to cut other osteotomy surfaces, so as to avoid the trackable element 3 from increasing the pose recognition error and/or failure of recognition due to the excessive rotation amplitude, and it can also avoid the large transmission error caused by the excessive change of the pose of the robotic arm, thereby further improving the positioning accuracy of the osteotomy guide tool. More preferably, the eccentric crank 403 is detachably connected to the osteotomy guide block 40, which facilitates different osteotomy guides by replacing the osteotomy guide block without the need for overall replacement, thereby reducing costs. Further, the eccentric crank 403 connects with the osteotomy guide block 40 via a quick-change interface. The present disclosure does not limit the structure of the quick-change interface.

As shown in FIG. 2, in one embodiment, the osteotomy guide tool 4 further includes a mounting base 402 for mounting the trackable element 3. The osteotomy guide block 40, the eccentric crank 403, the mounting base 402 and the mounting interface 401 are sequentially connected. In this embodiment, the mounting base 402 is provided with a target mounting hole 4021, and the trackable element 3 is mounted on the target mounting hole 4021, the number of target mounting holes 4021 is (but not limited to) two.

Figure 9:
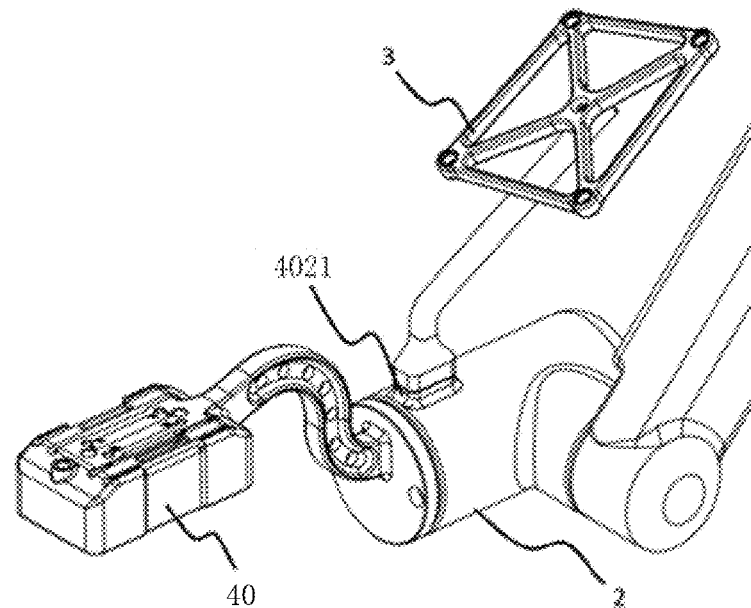
FIG. 9 is a schematic diagram of installing a trackable element on a housing of an end joint of a robotic arm according to an embodiment of the present disclosure.

As shown in FIG. 9, in an alternative embodiment, the mounting base 402 is optionally omitted, and the osteotomy guide block 40, the eccentric crank 403 and the mounting interface 401 are sequentially connected. At this time, the trackable element 3 is directly mounted on the shell of the end joint of the robotic arm 2, thereby simplifying the structure of the osteotomy guide tool 4, while keeping the trackable element 3 away from the surgical operation area, avoiding touching the target during the operation to affect the positioning. For example, a target mounting hole 4021 is provided on the shell of the end joint of the robotic arm 2 to facilitate the installation of the trackable element 3.

Continuing to refer to FIG. 2, in order to make the osteotomy guide tool 4 have multiple osteotomy guide operations, in the embodiment of the present disclosure, the osteotomy guide block 40 provides with the following guiding features:

femoral prosthesis mounting guiding hole 404; right leg pulley-osteotomy groove 405; left leg tibial-tooling positioning guiding hole 406; the first 0° guiding groove 407; the first 45° guiding groove 408; the second 45° guiding groove 410; the second 0° guiding grooves 411; left leg pulley-osteotomy groove 412; and right leg tibial-tooling positioning guiding hole 413.

In actual application, as long as the pose of the osteotomy guide tool 4 is adjusted by the robotic arm 2, it is enough to use the osteotomy guide tool 4 to provide guides for osteotomy and punching operations of the distal femur, the front of the femur, the back of the femur, the oblique of the front of the femur, the oblique of the femur, the pulley groove, the femoral prosthesis mounting hole, the tibial plateau, and the tibial keel treatment locating hole, and can be compatible with left and right legs, it makes the osteotomy operation of knee replacement easier and more convenient, and greatly reduces the operation time and improves the operation efficiency.

Figure 3:
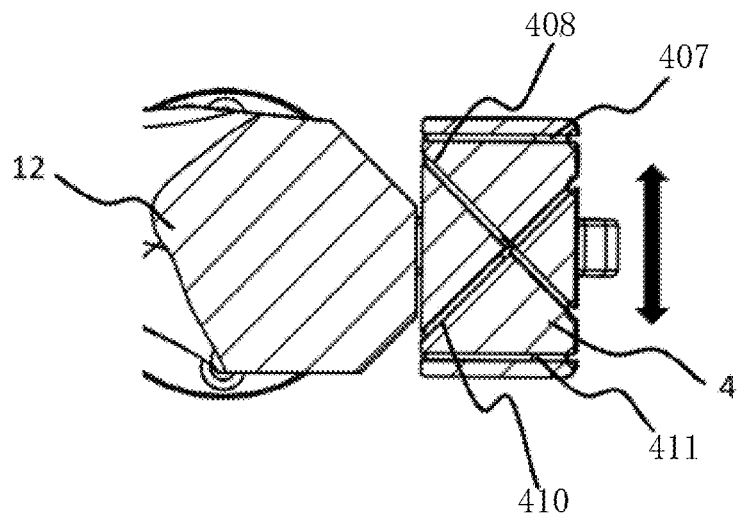
FIG. 3 is a schematic diagram of an osteotomy guide tool for translation to achieve multiple osteotomy guidance according to an embodiment of the present disclosure.

In addition, using the osteotomy guide tool 4 of this embodiment, as shown in FIG. 3, the osteotomy guide block 40 is provided with 0° guiding grooves (407 and 411) and 45° guiding grooves (408 and 410). When an osteotomy performed to the front of the femur, the oblique of the front of the femur, the oblique of the back of the femur, and the oblique of the back of the femur, it is enough for the translation (i.e., in the direction indicated by the arrow in FIG. 3) of the osteotomy guide tool to complete these osteotomy operations. Thus the trackable element 3 will not cause a large pose change, thereby reducing the transmission error of the robotic arm 2 and the target position tracking error, and improving the positioning accuracy.

Figure 4:
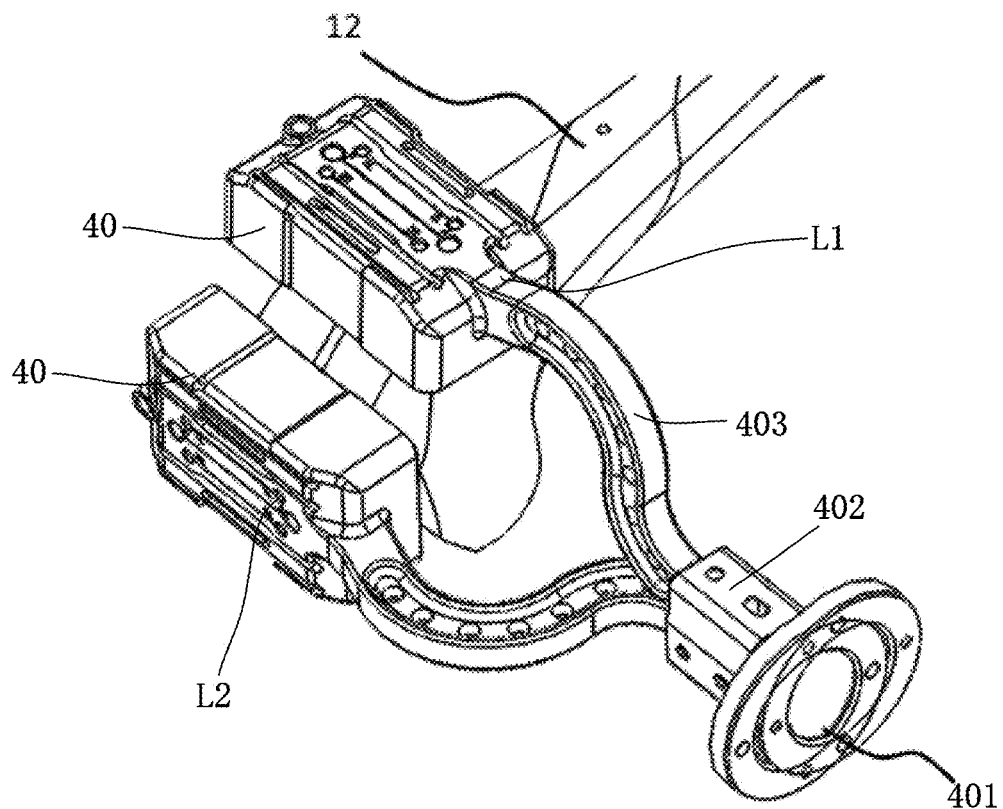
FIG. 4 is a schematic diagram of osteotomy surface adjustment by rotating the osteotomy guide tool according to an embodiment of the present disclosure.

In addition, with the osteotomy guide tool 4 of this embodiment, as shown in FIG. 4, due to the design of the eccentric crank 403, there is a certain offset between the rotation center of the osteotomy guide block 40 and the rotation center of the mounting interface 401. The rotation center of the osteotomy guide block 40 is close to the rotation center line of the end joint of the robotic arm (that is, the offset is not large). In this case, the robotic arm 2 only needs to perform a small linear displacement and rotation when adjusting the angle of the osteotomy guide tool 4 to cut other osteotomy surfaces. In more detail, when the osteotomy guide tool 4 is located at the position indicated by L1, an osteotomy for the tail end of the femur 12 can be operated by a surgical tool (such as a pendulum saw), and when the osteotomy guide tool 4 is located at the position indicated by L2, an osteotomy for the anterior/front and posterior/back ends of the femur 12 and the oblique of the femur can be performed with surgical tools. It should be noted that the offset is determined according to factors such as the type of prosthesis and the amplitude of movement of the osteotomy guide tool, and the size of the offset is not limited in the present disclosure.

Figure 5:
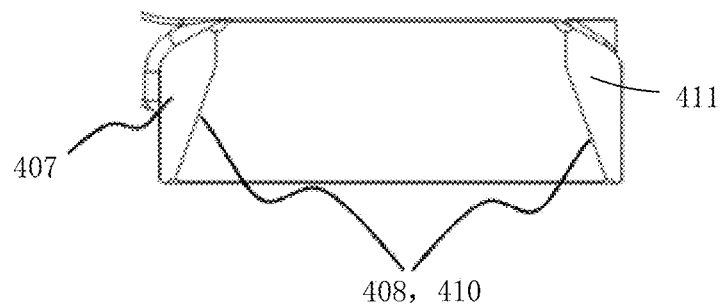
FIG. 5 is a cross-sectional view taken along the A-A line of the osteotomy guide tool shown in FIG. 2, where the 0° guiding groove has a shape of a horn.

In order to increase the scope of the prosthesis applicable to the osteotomy guide tool of the present disclosure, as shown in FIG. 5, the shape of the 0° guiding groove or the 45° guiding groove is preferably a horn, or preferably, the 0° guiding groove and the 45° guiding groove each has a shape of a horn, so as to increase the swing range of a surgical tool such as a pendulum saw in the guiding groove, so as to be compatible with osteotomy operations of more types of prostheses.

The orthopedic surgical system, in some embodiments, further includes a verification device, and the verification device is configured to identify the deformed state of one or both of the osteotomy guide tool 4 and the trackable element 3. When major deformation of the osteotomy guide tool 4 and/or the trackable element 3 is detected, the osteotomy guide tool 4 and/or the trackable element 3 can be replaced in time, or the relative position between the osteotomy guide tool 4 and the trackable element 3 can also be corrected by a correction device. The pose of the corrected osteotomy guide tool is replaced with the original recorded data, so that the movement of the robotic arm is controlled by the corrected pose of the osteotomy guide tool.

Figure 6:
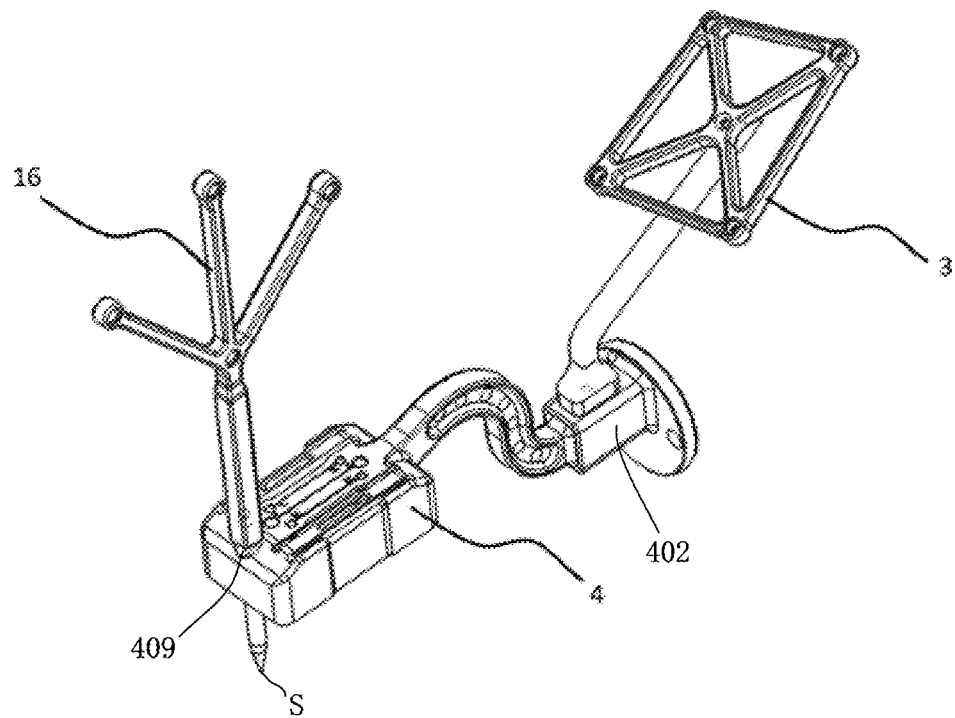
FIG. 6 is a schematic diagram of using a verification element to verify whether an osteotomy guide tool and/or a trackable element is deformed according to an embodiment of the present disclosure.

As shown in FIG. 6, the verification device includes at least one verification element 16 for removably mounting on the osteotomy guide block 40. For example, the osteotomy guide block 40 is provided with at least one verification hole 409, and the verification element 16 is mounted on the verification hole 409. Moreover, the verification element 16 has a step, and the stepped surface of the step is parallel to the surface of the osteotomy guide block 40. In this embodiment, the stepped surface is parallel to the upper surface of the osteotomy guide block 40 (parallel including matching), and the verification hole 409 is a through hole and is preferably opened vertically on the upper surface of the osteotomy guide block 40.

Further, in order to simplify the calculation process, most or all guiding features such as guiding grooves and guiding holes are provided on the upper surface of the osteotomy guide block 40. Furthermore, the axis of the verification hole 409 is located on the symmetry plane of the osteotomy guide block 40, and the end surface of the verification hole 409, the upper surface of the osteotomy guide block and the step surface are coplanarly arranged, so that the calculation process is simpler.

The specific verification process is as follows: first, the original position information of the verification element 16 (which has been mounted on the osteotomy guide block) relative to the trackable element 3 is recorded by the tracker 6 before leaving the factory. The tracker 6 records the current position information of the verification element 16 relative to the trackable element 3; the controller then determines whether the original position of the verification element matches the current position of the verification element; if the original position of the verification element matches the current position of the verification element, the osteotomy guide tool 4 and/or the trackable element 3 is determined by the controller as not deformed; if the original position of the verification element does not match the current position of the verification element, the osteotomy guide tool 4 and/or the trackable element 3 is determined by the controller the controller as deformed In this embodiment, the position information of the verification element 16 relative to the trackable element 3 includes: the position and the pose of the front end point of the verification element in the coordinate system of the trackable element. As shown in FIG. 6, the front end point of the verification element 16 is the tip S of the verification element 16. In use, if the controller determines that the current position information of the front end point of the verification element does not match the original information recorded at the factory, it can be determined that one or both of the osteotomy guide tool 4 and the trackable element 3 are deformed. This is because whether the trackable element or the osteotomy guide tool 4 is deformed, the deformation is transmitted to the verification hole 409. If the verification hole 409 is deformed, the deformation can be identified by the verification element.

Figure 7:
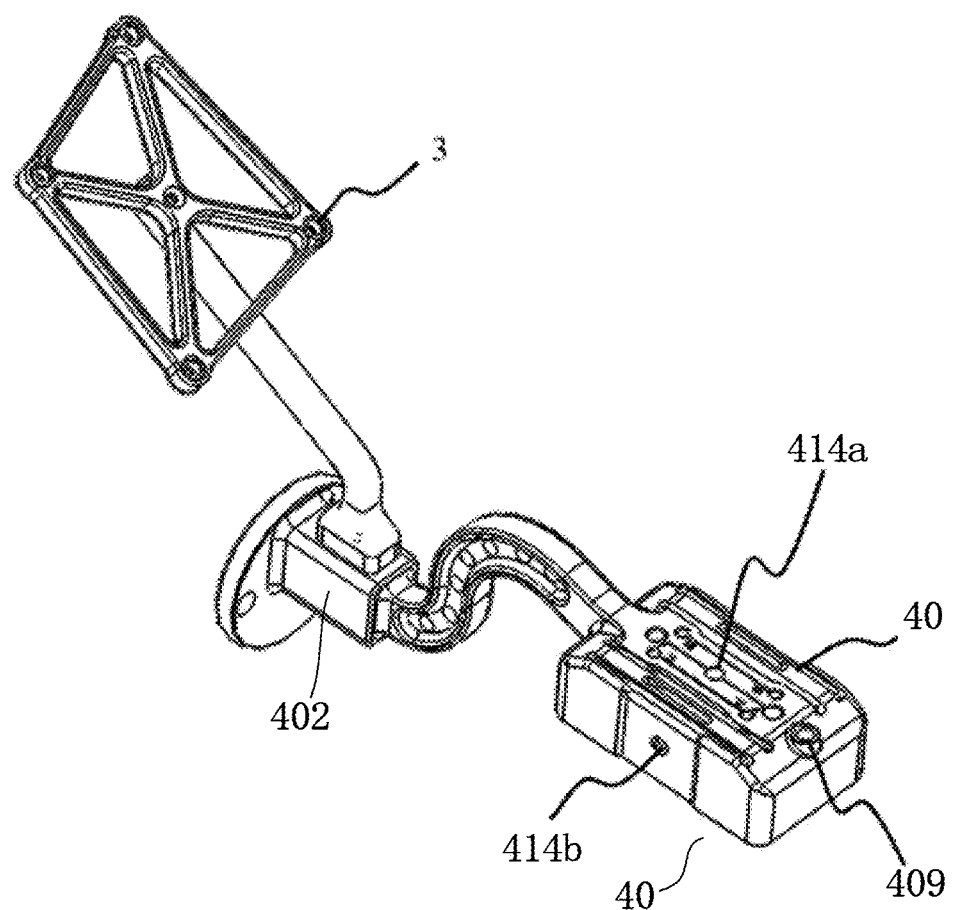
FIG. 7 is a schematic structural diagram of an osteotomy guide tool provided with a correction hole according to an embodiment of the present disclosure.
Figure 8:
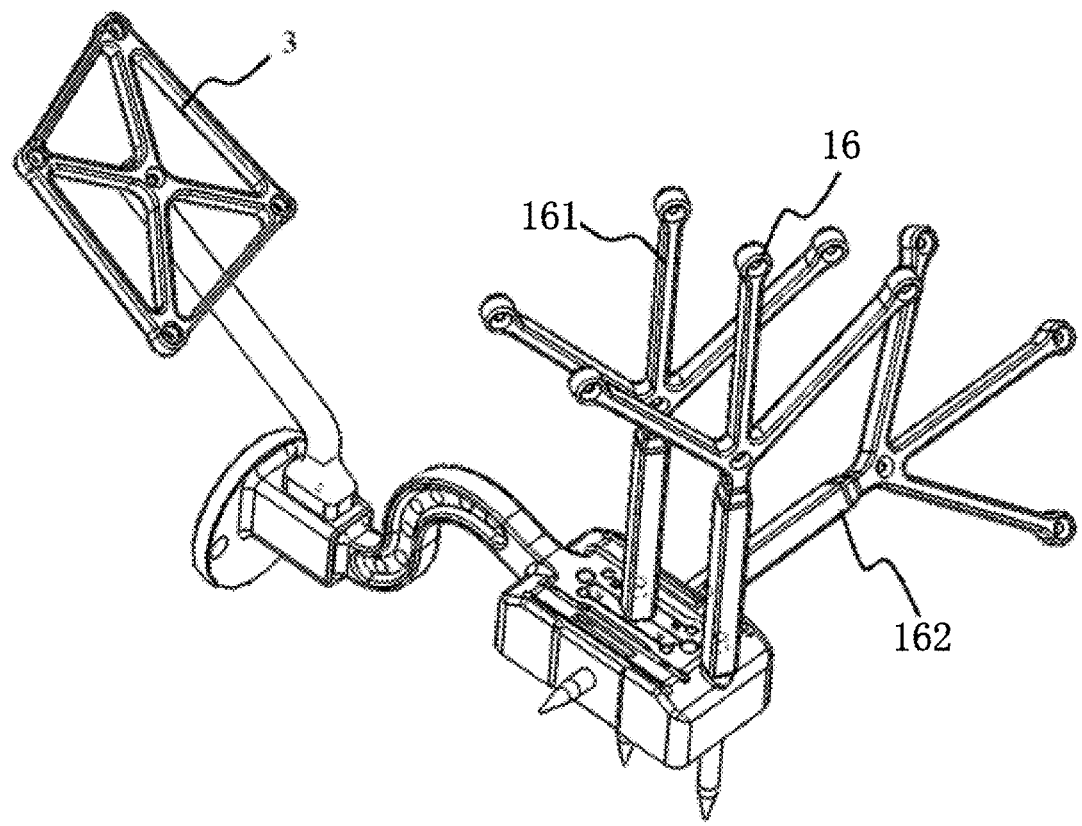
FIG. 8 is a schematic diagram of correcting an osteotomy guide tool by using a correction element according to an embodiment of the present disclosure.

The orthopedic surgical system preferably further includes a correction device, when the verification device recognizes that at least one of the osteotomy guide tool 4 and the trackable element 3 is deformed, the correction device is configured to correct the relative position between the osteotomy guide tool 4 and the trackable element 3, and the controller updates the posture mapping relationship between the osteotomy guide tool 4 and the trackable element 3 accordingly. As shown in FIG. 7 and FIG. 8, the verification device includes at least two correction elements, and the at least two correction elements are detachably mounted on the osteotomy block 40. Further, a verification element 16 can be selected as the correction element. In this embodiment, the relative positions between the osteotomy guide tool 4 and the trackable element 3 are corrected by two correction elements 161 and 162.

In more detail, when calibrating, firstly, the tracker 6 records the positions of two of the correction elements 161 and 162 relative to the trackable element 3 respectively; then, the controller calculates the current position information of the osteotomy guide tool 4 relative to the trackable element 3 based on the position information of the two of the correction elements 161 and 162 relative to the trackable element 3, and updates the posture mapping relationship between the osteotomy guide tool 4 and the trackable element 3 accordingly.

Further, the position of the correction element 161 relative to the trackable element 3 is recorded as $T_1$ and record the position of the correction element 162 relative to the trackable element 3 as $T_2$. Where $T_1$ represents the position of the correction element 161 in the coordinate system of the trackable element; $T_2$ represents the position of the correction element 162 in the coordinate system of the trackable element.

In this embodiment, during the calibration process, the position information of the osteotomy guide tool 4 relative to the trackable element 3 is obtained in the following manner:

first, according to the position $T_1$ and $T_2$ of the two correction elements 161 and 162 in the coordinate system of the trackable element, the controller obtains: the position $T_0$ of the center point of the osteotomy guide block 40 in the coordinate system of the trackable element; and the position $T_3$ of the surface of the osteotomy guide block 40 (the surface matching the aforementioned stepped surface, such as the upper surface) in the coordinate system of the trackable element;

further, according to the position $T_0$ of the center point of the osteotomy guide block and the position $T_3$ of the surface of the osteotomy guide block in the coordinate system of the trackable element, then the controller obtains the position and the pose of the osteotomy guide tool 4 relative to the trackable element 3.

After obtaining the position and the pose of the corrected osteotomy guide tool 4 relative to the trackable element 3, the original position information recorded at the factory can be replaced accordingly. During the operation, the position of the osteotomy guide tool is tracked with the corrected position information and the movement of the robotic arm is controlled, thereby achieving accurate positioning of the osteotomy guide tool. Preferably, the control device further includes a storage device for storing a posture mapping relationship between the trackable element 3 and the osteotomy guide tool 4. In addition, the navigation device and the control device can be integrated to form a navigation system.

As shown in FIG. 7, the osteotomy guide block 40 is provided with at least two correction holes. In some embodiments, the correction hole 409 may constitute one correction hole. In this embodiment, in addition to the verification hole 409, two other correction holes are provided, namely a first correction hole 414a and a second correction hole 414b. The position of the correction hole is not particularly limited in the present disclosure, and is provided on the same surface or on different surfaces. The verification elements 16 (i.e., two correction elements) are mounted in any two holes of the first correction hole 414a, the second correction hole 414b and the correction hole 409. The position of the two holes where the two correction elements are located can be obtained by matching the step surface on the two verification elements 16 with the upper surface of the osteotomy guide tool. The orientation of each guiding groove and the guiding hole of the osteotomy guide tool relative to the trackable element can be calculated, so as to correct the position of the guide tool relative to the trackable element. In some embodiments, the end surface of each of the correction holes, the upper surface of the osteotomy guide block and the step surface of the correction element are coplanarly disposed, thereby simplifying the calculation process and improving the correction efficiency.

In this embodiment, the position of each correction element in the coordinate system of the trackable element includes: the position and the pose of the front end point of the correction element in the coordinate system of the trackable element; and the position and the pose of the step surface of the target in the coordinate system of the trackable element.

Figure 10:
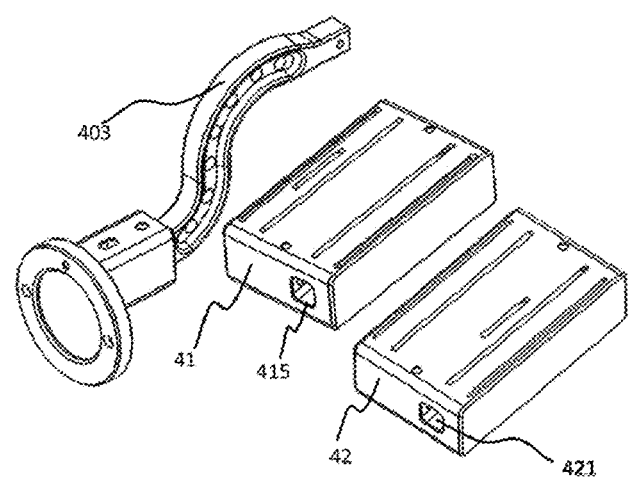
FIG. 10 is a schematic structural diagram of an osteotomy guide with two mirror configurations provided by an embodiment of the present disclosure.

Further, in order to balance the osteotomy operation of the left and right legs, the osteotomy guide block 40 has an axisymmetric structure. In an alternative embodiment, as shown in FIG. 10, two osteotomy guides mirrored to each other can also be provided, which are osteotomy guide blocks 41 and 42, respectively. The osteotomy guide block 41 can achieve osteotomy guidance of the left leg. The osteotomy guide block 42 can achieve osteotomy guidance of the right leg. Each osteotomy guide block is connected to the eccentric crank 403 via a quick-change interface, which is convenient for disassembly. In this embodiment, the osteotomy guide block 41 is connected to the eccentric crank 403 via a quick-change interface 415, and the osteotomy guide block 42 is connected to the eccentric crank 403 via a quick-change interface 421. Optionally, the positions of the two quick-change interfaces 415 and 421 are designed as corresponding configuration instead of mirror configuration.

Figure 11:
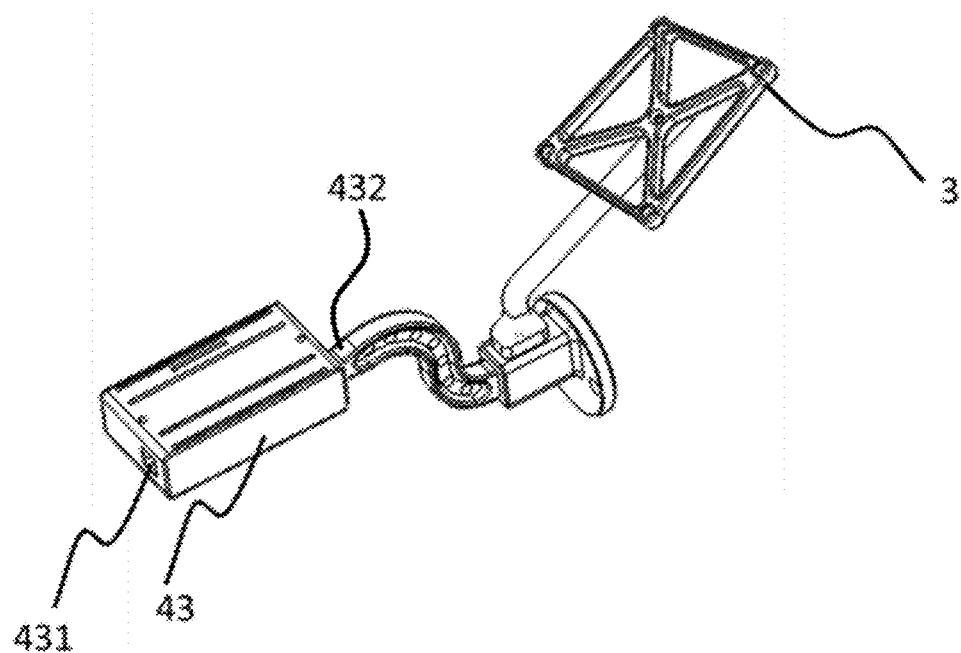
FIG. 11 is a schematic diagram of providing two quick-change interfaces on the same osteotomy guide block to achieve osteotomy of left and right legs according to an embodiment of the present disclosure.
Figure 13:
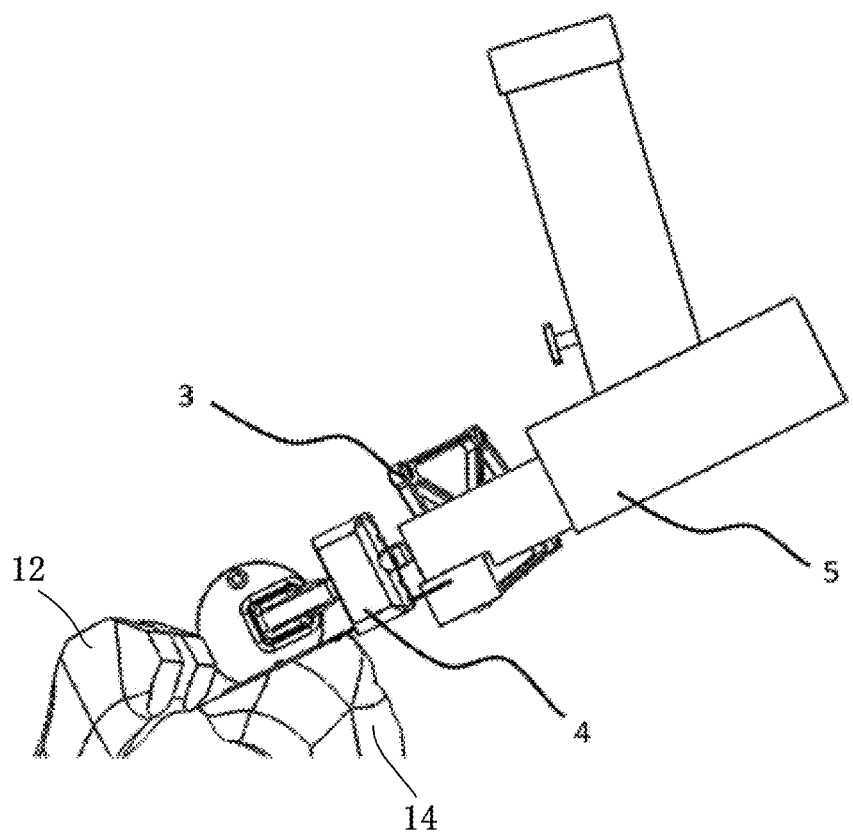
FIG. 13 is a schematic diagram of guiding the osteotomy of a tibial plateau according to an embodiment of the present disclosure.
Figure 14:
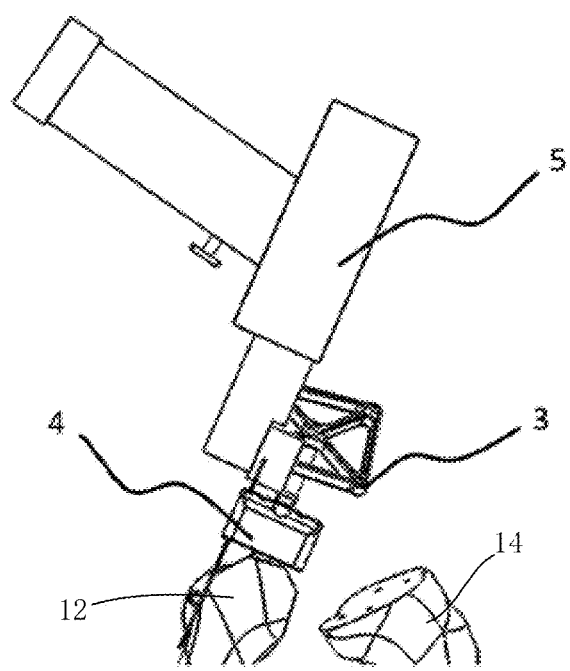
FIG. 14 is a schematic diagram of guiding the osteotomy of the front end of the femur according to an embodiment of the present disclosure.

As shown in FIG. 11, in other embodiments, only one osteotomy guide block 43 is provided. The osteotomy guide block 43 is provided with two quick-change interfaces 431 and 432, and the two quick-change interfaces 431 and 432 are provided on two opposite sides of the osteotomy guide block 43. The eccentric crank 403 is selectively detachably connected to one of the two quick-change interfaces 431 and 432. The eccentric crank 403 is connected to different quick-change interfaces on the same osteotomy guide block, and can be used for knee osteotomy of the left leg and the right leg, respectively. However, the present disclosure does not limit the relative positions of the two quick-change interfaces 431 and 432, they can be on opposite surfaces, and the axes can be collinear. Optionally, the osteotomy guide block 43 is also provided with a quick-change interface. The osteotomy guide block 43 is connected to the eccentric crank 403 after being turned 180°, so that the osteotomy guide block 43 can also be used for the osteotomy operation of the left and right legs. In short, the osteotomy operation of the left and right legs can be realized by only one osteotomy guide block, and the osteotomy operation of the left and right legs can also be implemented by two osteotomy guide blocks, which is not limited in the present disclosure. Of course, it is optionally to use the same osteotomy guide block to complete the osteotomy operation of the left and right legs. Taking the left leg as an example, as shown in FIG. 13, when the osteotomy guide tool 4 provided by the present disclosure is applied, it can provide guidance for the osteotomy operation of the tibial plateau. As shown in FIG. 14, the osteotomy guide tool 4 of the present disclosure can also provide guidance for femoral osteotomy, so there is no need to change the osteotomy guide during the operation, which is more convenient and efficient.

In this embodiment, the controller can provide a desired moving path composed of a plurality of positioning points, and the controller is configured to control the movement of the robotic arm 2 to drive the osteotomy guide tool 4 and the trackable element 3 to move, until the trackable element 3 is moved to the desired position along the desired moving path, thereby further improving the accuracy of positioning. Further, the controller obtains a desired moving path of the trackable element according to the current position and the desired position of the trackable element 3. Wherein, the controller determines a desired position of the trackable element 3 according to a posture mapping relationship between the trackable element and the osteotomy guide tool, and a target position of the osteotomy guide tool.

Figure 12:
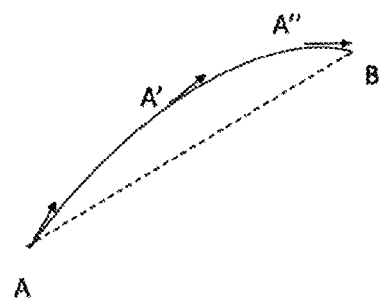
FIG. 12 is a schematic diagram of a moving path of a trackable element according to an embodiment of the present disclosure.

In more detail, as shown in FIG. 12, when the osteotomy operation is started, the controller first obtains the current position A of the trackable element 3 according to the registration information of the robotic arm 2 (including the posture mapping relationship between the trackable element and the osteotomy guide tool). The desired position B of the trackable element 3 can be obtained based on human bone registration information (such as correlation information between the three-dimensional knee joint digital model and the CT/MR scan image) and the application of prosthetic information. Furthermore, according to the principle of inverse kinematics, the desired moving path of the trackable element trackable element 3 can be planned. The controller sends instructions to the actuators of joints on each robotic arm to control the movement of the trackable element 3 through the movement of the robotic arm joint. During the movement, the tracker 6 tracks and feeds back the real positions A' and A" of the trackable element 3 in real time which then sent to the controller. The controller can calculate the deviation between the real-time position of the trackable element 3 and the desired position, thereby updating the moving path of the trackable element 3, and finally controlling the trackable element 3 to move to the desired position B, thereby achieving precise positioning/locating of the osteotomy guide tool 4.

Next, the guiding features on the osteotomy guide will be further described in combination with specific embodiments.

Figure 15:
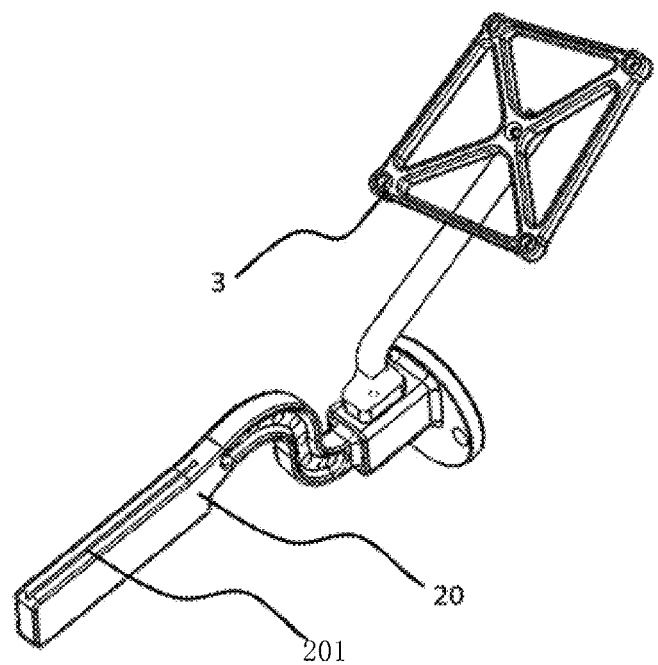
FIG. 15 is a schematic structural diagram of an osteotomy guide tool provided with a single 0° guiding groove according to a first embodiment of the present disclosure.

As shown in FIG. 15, in a first embodiment, an osteotomy guide tool is provided, which includes an osteotomy guide block 20 that can be used for osteotomy guidance of the distal femur and the tibial plateau. Specifically, the guiding feature on the osteotomy guide block 20 only includes a 0° guiding groove 201 which is opened on the upper surface of the osteotomy guide block 20, and the osteotomy of the distal femur and tibial plateau can be achieved by rotating the osteotomy guide tool. It should be known that in this article, the 0° guiding groove means that the opening direction of the guiding groove is parallel to one side of the osteotomy guide block and the angle is 0°, for example, when the 0° guiding groove penetrates the upper and lower surfaces of the osteotomy guide block. Similarly, the 45° guiding groove refers to the case where the angle between the opening direction of the guiding groove and the side of the osteotomy guide are at 45°, for example, when the 45° guiding groove penetrates the upper and lower surfaces of the osteotomy guide from top to bottom.

Figure 16:
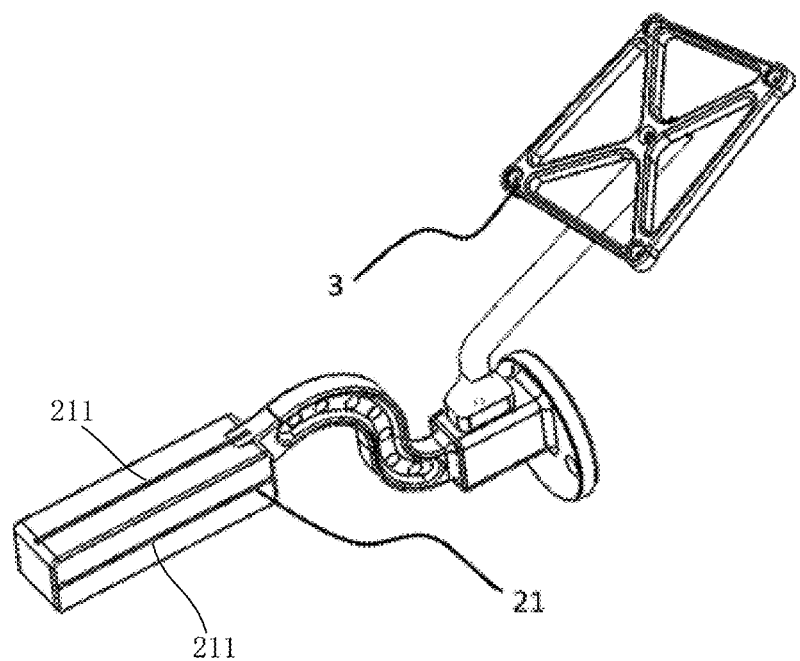
FIG. 16 is a schematic structural diagram of an osteotomy guide tool provided with two 0° guiding grooves according to a second embodiment of the present disclosure.

As shown in FIG. 16, in a second embodiment, a guide tool is provided, which includes an osteotomy guide block 21 that can be used for osteotomy guidance of the distal femur and the tibial plateau. The guiding features on the osteotomy guide block 21 include two 0° guiding grooves 211 arranged on different sides of the osteotomy guide block 21, for example, one on the upper surface and the other one on the side adjacent to the upper surface. The two 0° guiding grooves 211 are arranged around the rotation axis of the osteotomy guide block 21. This configuration can reduce the rotation angle of the surgical tool 5 when cutting different osteotomy schemes, avoid large identification deviation of the target amplitude of movement, and avoid large transmission errors caused by excessive changes in the pose of the robotic arm.

Figure 17:
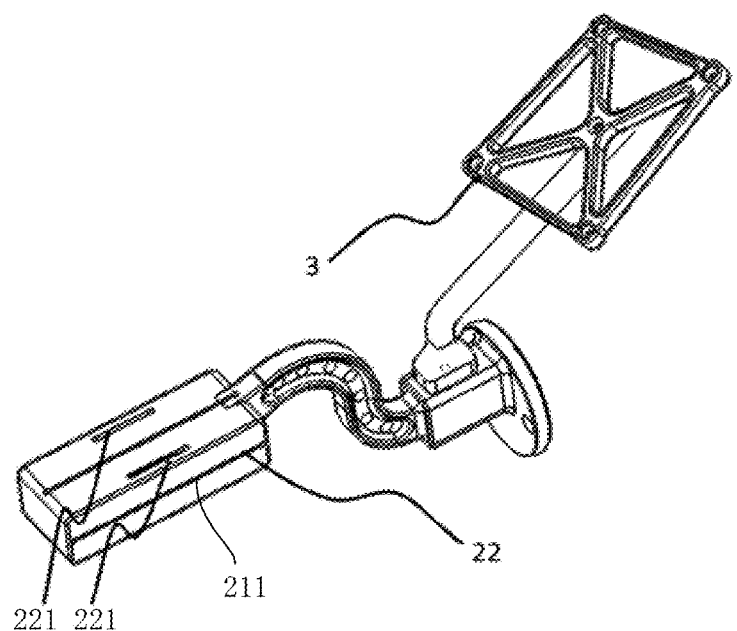
FIG. 17 is a schematic structural diagram of an osteotomy guide tool provided with two pulley-osteotomy grooves and two 0° guiding grooves according to a third embodiment of the present disclosure.

As shown in FIG. 17, in a third embodiment, an osteotomy guide tool is provided, which includes an osteotomy guide block 22, which can be used for osteotomy guidance of the distal femur, the tibial plateau and the pulley groove. Specifically, on the basis of the osteotomy guide block 21 of the second embodiment, two pulley-osteotomy grooves 221 are added to realize the osteotomy of the left and right legs.

Figure 18:
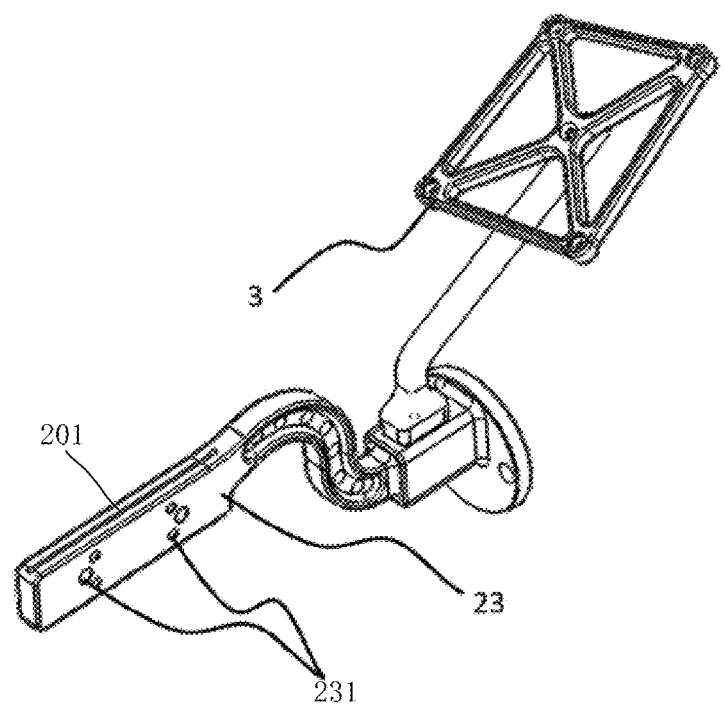
FIG. 18 is a schematic structural diagram of an osteotomy guide tool provided with a single 0° guiding groove and two guiding holes according to a fourth embodiment of the present disclosure.

As shown in FIG. 18, in a fourth embodiment, an osteotomy guide tool is provided, which includes an osteotomy guide block 23, which can be used for osteotomy guidance of the distal femur and the tibial plateau. Based on the osteotomy guide block 20 of the first embodiment, a plurality of guiding holes 231 (such as two guiding holes 231) are added, and the plurality of the guiding holes 231 can be used for guiding the femoral prosthesis mounting hole and the tibial tool mounting hole.

Figure 19:
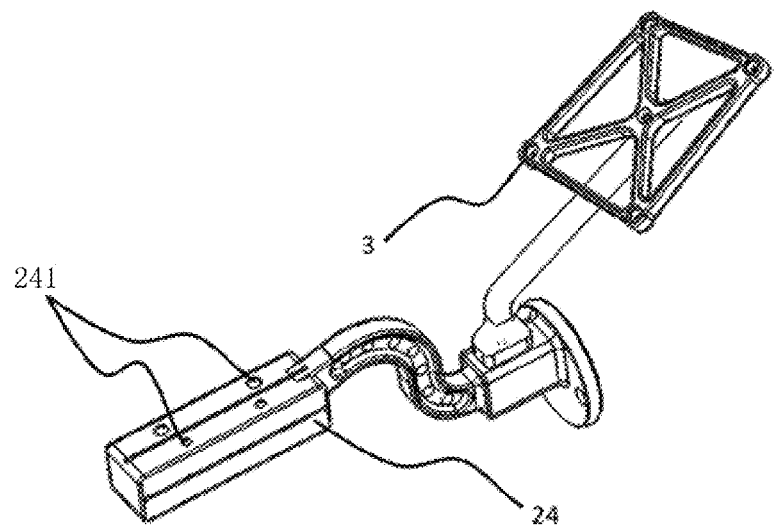
FIG. 19 is a schematic structural diagram of an osteotomy guide tool provided with two 0° guiding grooves and two guiding holes according to a fifth embodiment of the present disclosure.

As shown in FIG. 19, in a fifth embodiment, an osteotomy guide tool is provided, which includes an osteotomy guide block 24, which can be used for osteotomy guidance of the distal femur and the tibial plateau. In addition to the two guiding grooves in the second embodiment, the osteotomy guide tool further includes guiding holes 241 (such as two guiding holes 241), which can be used for guidance of the femoral prosthesis mounting hole and the tibial tool mounting hole.

Figure 20:
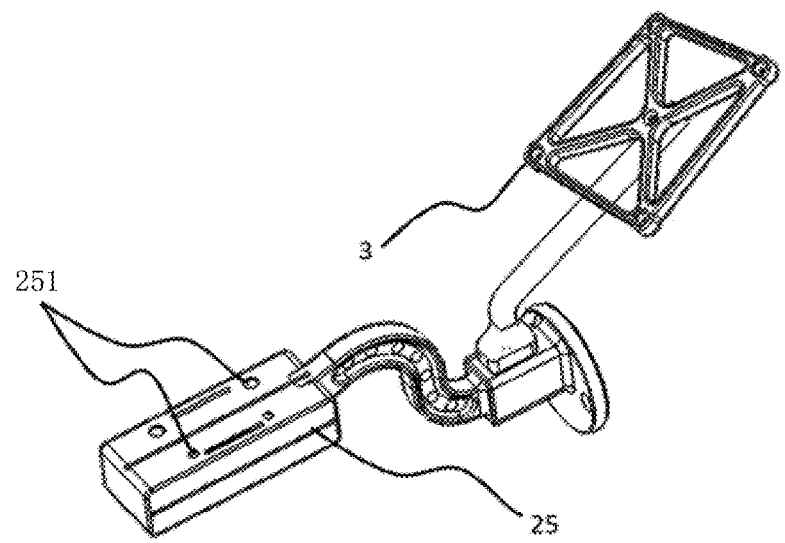
FIG. 20 is a schematic structural diagram of an osteotomy guide tool provided with two 0° guiding grooves, two pulley-osteotomy grooves and two guiding holes according to a sixth embodiment of the present disclosure.

As shown in FIG. 20, in a sixth embodiment, an osteotomy guide tool is provided, which includes an osteotomy guide block 25, and a plurality of guiding holes 251 (such as two guiding holes) are added, relating to the osteotomy guide tool in the third embodiment, so that the osteotomy guide block 25 can be used for osteotomy guidance of the distal femur, the tibia plateau and the pulley groove, and can also be used for guidance of femoral prosthesis mounting holes and tibial tool mounting holes.

Figure 21:
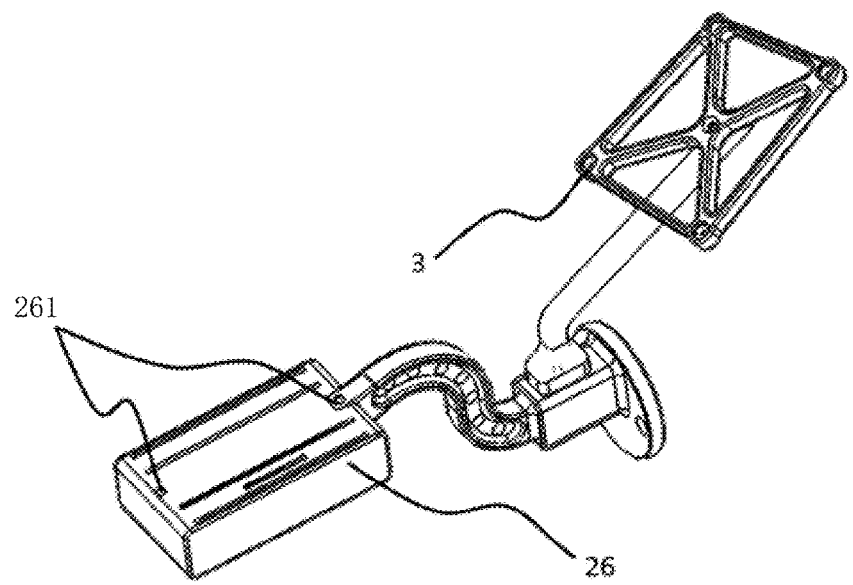
FIG. 21 is a schematic structural diagram of an osteotomy guide tool provided with two fixing holes and multiple guiding grooves according to a seventh embodiment of the present disclosure.

As shown in FIG. 21, in a seventh embodiment, an osteotomy guide tool is provided, which includes an osteotomy guide block 26. The osteotomy guide block 26 includes a locating hole 261 in addition to necessary guiding features. After the robotic arm 2 places the osteotomy guide tool at a predetermined position, the positioning nail can be used to fix the osteotomy guide tool to the bone through the locating hole 261 on the osteotomy guide block 26. Then, the anterior/front end of the femur, the oblique of the front end of the femur, the posterior/back end of the femur, the oblique of the back end of the femur, and the pulley groove are cut at once. The method can avoid the movement of the osteotomy guide tool due to the insufficient rigidity of the robotic arm during the operation and reduce the guide deviation.

Figure 22:
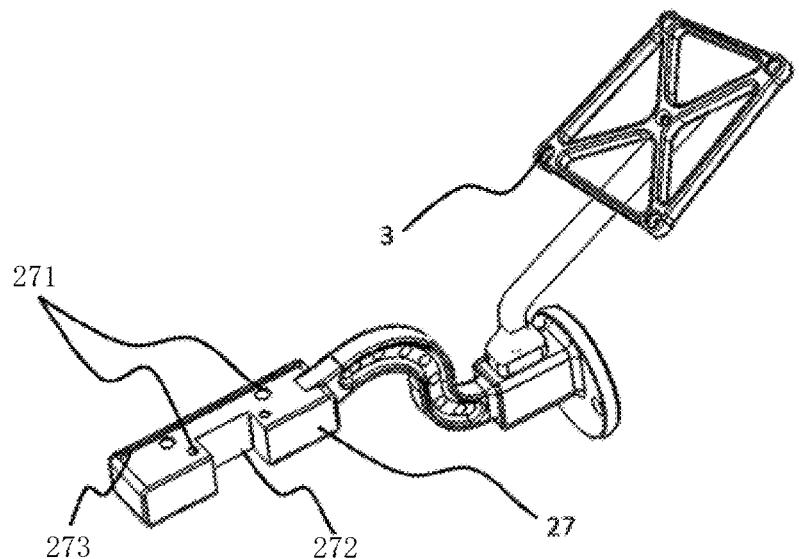
FIG. 22 is a schematic structural diagram of an osteotomy guide tool provided with a square pulley-osteotomy grooves, a long guiding groove and two guiding holes according to an eighth embodiment of the present disclosure.

As shown in FIG. 22, in an eighth embodiment, an osteotomy guide tool is provided, which includes an osteotomy guide block 27. The osteotomy guide block 27 is a modified structure of the osteotomy guide tool with two guide grooves and two guiding holes in the fifth embodiment. In the modified structure, the square groove 272 is used for osteotomy guide of the pulley groove, the long guiding groove 273 is used to cut other osteotomy surfaces of the femur and the tibia, and the guiding hole 271 is used for guidance of the femoral prosthesis mounting hole and the tibial tool mounting hole.

Figure 23:
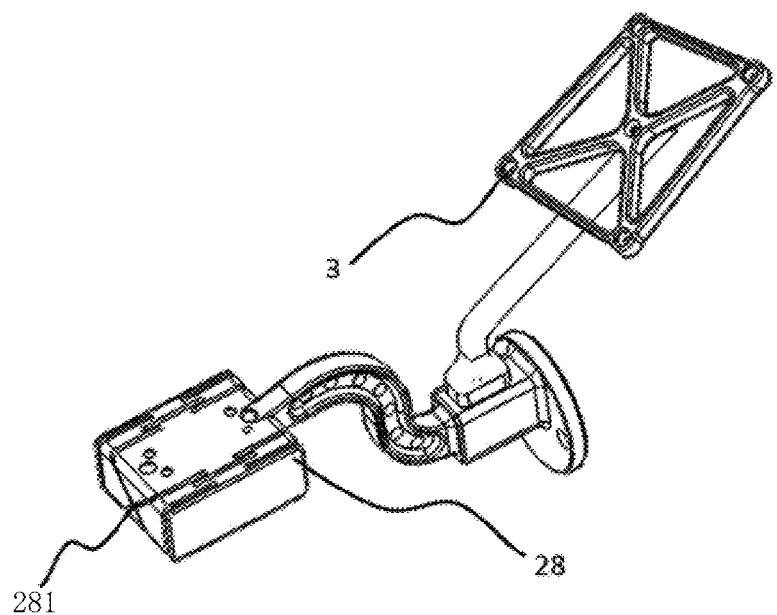
FIG. 23 is a schematic structural diagram of an osteotomy guide tool after opening a side of a guiding groove according to a ninth embodiment of the present disclosure.

As shown in FIG. 23, in a ninth embodiment, an osteotomy guide tool is provided, which includes an osteotomy guide block 28, and one or both sides of a guiding groove on the osteotomy guide block 28 form a breach 281. The guiding groove with a breach can be a 0° guiding groove or a 45° guiding groove. The surgical tool 5 (such as a swing saw) can be swung in a wide range along the breach 281, so that the length of the osteotomy guide block can be reduced. This form can reduce the requirements for surgical wounds and reduce damage to patient tissues. It should be known that the "breach" refers to that one or both ends of the guiding groove extend to the surface of the osteotomy guide block and penetrate the surface to form a guiding groove that is open on one or both sides thereof.

Figure 24:
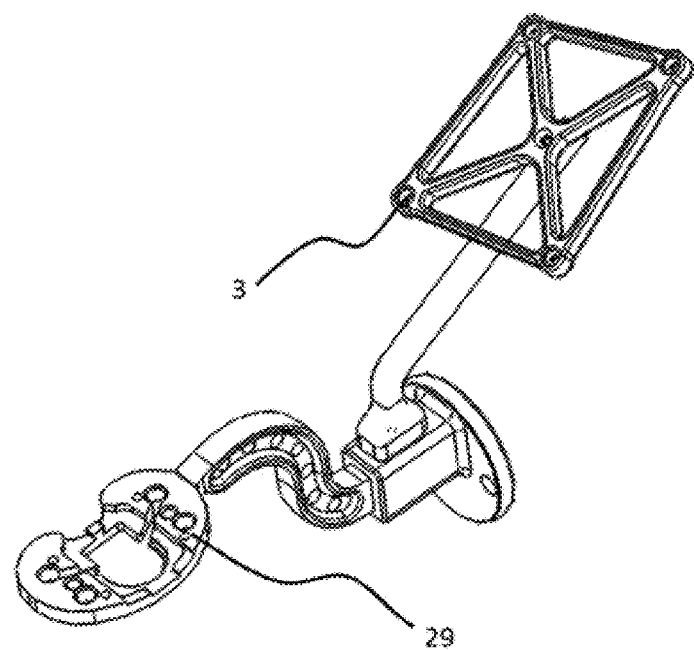
FIG. 24 is a schematic structural diagram of a tibial treatment tool directly used as an osteotomy guide tool provided by a tenth embodiment of the present disclosure.
Figure 25:
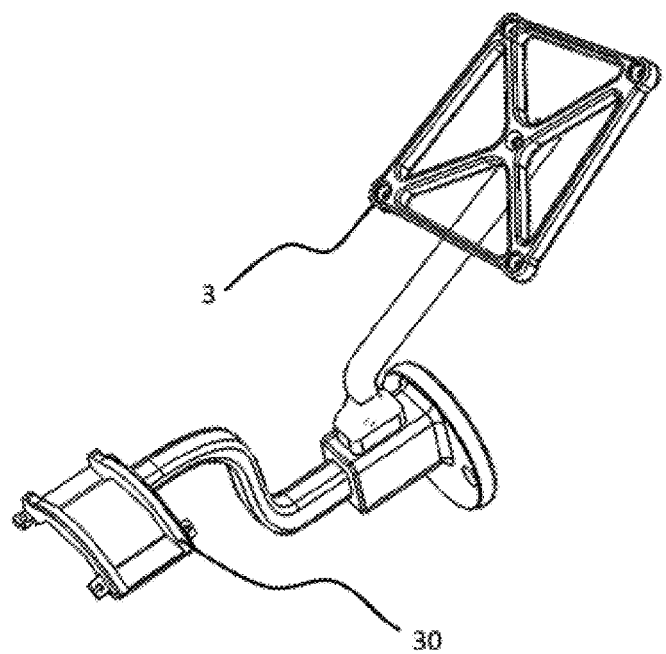
FIG. 25 is a schematic structural diagram of a pulley groove guide tool directly used as an osteotomy guide tool provided by an eleventh embodiment of the present disclosure.

As shown in FIG. 24, in a tenth embodiment, an osteotomy guide block 29 is provided. Unlike the foregoing, a tibial treatment tool can be used as the osteotomy guide block 29 to realize automatic positioning of the tibial treatment tool. As shown in FIG. 25, in an eleventh embodiment, an osteotomy guide tool is provided, which includes an osteotomy guide block 30. Unlike the foregoing, a pulley-osteotomy guide tool is used as the osteotomy guide block 30 to realize the automatic positioning of the pulley-osteotomy guide tool.

Therefore, different combinations of guiding features can be provided on the osteotomy guide block according to the requirements of the present disclosure. In some embodiments, a guiding groove and a guiding hole are simultaneously provided on the osteotomy guide block, but the number and position of the guiding grooves on the osteotomy guide block are not limited. Similarly, the number and position of the guiding holes are not limited. One or more or any combinations of 0° guiding grooves, 45° guiding grooves and pulley-osteotomy grooves can be provided on the osteotomy guide block. One or more or any combinations of femoral prosthesis mounting guiding holes, left leg tibial-tooling positioning guiding holes, right leg tibial-tooling positioning guiding holes, and osteotomy-guide fixing holes can be provided on the osteotomy guide block.

FIG. 26a provides a sterile bag 31, but for clarity, only a portion of the sterile bag 31 used by the robotic arm is shown. By putting a sterile bag 31 on the end joint of the robotic arm, one end of the sterile bag 31 covers a connection port (such as a flange) of a robotic arm, and the connection port is detachably connected to the osteotomy guide tool. In this way, the surgical area can be isolated to ensure aseptic operation of the surgical environment. Preferably, a portion of the end of the sterile bag 31 connected to the flange of the robotic arm is made of a material with a certain hardness, for example, medical plastic such as PEEK can be selected. In addition, a corresponding yielding hole 311 is provided to avoid the fasteners 312 on the osteotomy guide tools, such as screws and positioning pins. The sterile bag 31 can meet the installation requirements of the surgical tool and minimize the exposure of the bacterial part of the robotic arm.

Further, an embodiment of the present disclosure further provides a computer-readable storage medium that can store an instruction, and when the instruction is executed by a processor, the steps of the method performed by the controller are performed.

The preferred embodiments of the present disclosure are as described above, but are not limited to the scope disclosed in the above embodiments. For example, the present disclosure does not limit the number and types of guiding features on the osteotomy guide block. If the orthopedic surgery system is applied to other orthopedic operations, the types of guiding grooves and guiding holes are different from those listed above. In addition, the present disclosure does not limit the position of the verification hole and the position of the correction hole. In addition, The guiding hole is preferably opened on the same surface of the osteotomy guide block, so as to ensure the accuracy of the guidance and reduce the thickness of the osteotomy guide block, and the above targets are preferably optical targets for emitting optical signals.

The above description is only a description of the preferred embodiments of the present disclosure, and does not limit the scope of the present disclosure. Any changes or modifications made by those skilled in the art according to the above disclosure shall fall within the protection scope of the claims.

What is claimed is:

1. A method for correcting a position of an osteotomy guide tool, comprising:
controlling a movement of a robotic arm according to a current position and a desired position of a trackable element, the trackable element mounted on the osteotomy guide tool or on the robotic arm, so that the robotic arm drives the osteotomy guide tool and the trackable element to move, until the trackable element is moved to the desired position; wherein a position information of the trackable element is used to represent a position of the osteotomy guide tool; said osteotomy guide further comprising, before the controlling step, a verificating step for detecting whether the osteotomy guide tool and/or the trackable element is deformed, wherein the verificating step comprises: determining whether an original position of a verification element matches a current position of the verification element based on: 1) the original position of the verification element mounted on the osteotomy guide tool relative to the trackable element before leaving a factory, and 11) the current position of the verification element relative to the trackable element during use of the osteotomy guide tool; determining that the osteotomy guide tool and/or the trackable element is not deformed if the original position of the verification element matches the current position of the verification element, and proceeding to the controlling step of controlling the movement of the robotic arm according to the current position and the desired position of the trackable element mounted on the osteotomy guide tool or on the robotic arm; and determining that the osteotomy guide tool and/or the trackable element 1s deformed if the original position of the verification element does not match the current position of the verification element, and correcting a relative position between the osteotomy guide tool and the trackable element before proceeding to the controlling step of controlling the movement of the robotic arm according to the current position and the desired position of the trackable element mounted on the osteotomy guide tool or on the robotic arm.

2. The method for correcting a position of an osteotomy guide tool of claim 1, wherein the correcting step comprises:
acquiring positions of at least two correction elements mounted on the osteotomy guide tool relative to the trackable element; and
obtaining a current position of the osteotomy guide tool relative to the trackable element according to the positions of the at least two correction elements relative to the trackable element, and updating the relative position between the osteotomy guide tool and the trackable element.

3. The method for correcting a position of an osteotomy guide tool of claim 2, wherein the positions of two of the correction elements relative to the trackable element are recorded as $T_1$ and $T_2$ where $T_1$ represents a position of a first correction element in a coordinate system of the trackable element, and $T_2$ represents a position of a second correction element in the coordinate system of the trackable element;
wherein the current position of the osteotomy guide tool relative to the trackable element is obtained by:
obtaining a position $T_0$ of a center point of an osteotomy guide block and a position $T_3$ of a surface of the osteotomy guide block in the coordinate system of the trackable element, according to the positions $T_1$ and $T_2$ of the at least two correction elements in the coordinate system of the trackable element; and
obtaining a position and a pose of the osteotomy guide tool relative to the trackable element according to the position $T_0$ of the center point of the osteotomy guide block and the position $T_3$ of the surface of the osteotomy guide block in the coordinate system of the trackable element.

4. The method for correcting a position of an osteotomy guide tool of claim 3, wherein the position of each of the correction elements in the coordinate system of the trackable element comprises:
a position and a pose of a front end of the correction element in the coordinate system of the trackable element; and
a position and a pose of a stepped surface of the correction element in the coordinate system of the trackable element;
wherein the correction element has a step, and the stepped surface of the step is parallel to a surface of the osteotomy guide block.

5. The method for correcting a position of an osteotomy guide tool of claim 1, further comprising, before the controlling step:
determining a desired moving path of the trackable element according to the current position and the desired position of the trackable element;
wherein during the controlling step, the robotic arm is controlled to move the trackable element from the current position to the desired position along the desired moving path.

6. The method for correcting a position of an osteotomy guide tool of claim 5, wherein the desired position of the trackable element is obtained according to a posture mapping relationship between the trackable element and the osteotomy guide tool, as well as a target position of the osteotomy guide tool.

7. The method for correcting a position of an osteotomy guide tool of claim 6, wherein the posture mapping relationship between the trackable element and the osteotomy guide tool comprises a posture mapping relationship between multiple feature points on the osteotomy guide tool and the trackable element.

8. The method for correcting a position of an osteotomy guide tool of claim 7, wherein the posture mapping relationship between each of the multiple feature points and the trackable element is obtained by:
  acquiring relative positions between respective target balls on the trackable element, and establishing a coordinate system of the trackable element according to the acquired relative positions;
  acquiring a position of a center point of an osteotomy guide block in the coordinate system of the trackable element; and
  determining a position and a pose of the multiple feature points in the coordinate system of the trackable element according to positions of the multiple feature points relative to the center point of the osteotomy guide, as well as a position of the center point of the osteotomy guide in the coordinate system of the trackable element.

9. The method for correcting a position of an osteotomy guide tool of claim 1, wherein a position information of the verification element relative to the trackable element comprises: a position and a pose of a front end of the verification element in a coordinate system of the trackable element.

\* \* \* \* \*